US010765376B2

(12) United States Patent
Brown, III et al.

(10) Patent No.: US 10,765,376 B2
(45) Date of Patent: Sep. 8, 2020

(54) METHOD AND APPARATUS TO DIAGNOSE THE METASTATIC OR PROGRESSIVE POTENTIAL OF CANCER, FIBROSIS AND OTHER DISEASES

(71) Applicant: University of Rochester, Rochester, NY (US)

(72) Inventors: Edward Bernard Brown, III, Honeoye Falls, NY (US); Seth Warrington Perry, Pittsford, NY (US); Kathleen Anne Burke, Rockville Centre, NY (US); Robert Matthew Kottmann, Rochester, NY (US); Patricia Janet Sime, Pittsford, NY (US); Jesse Wakefield Sharp, Rochester, NY (US)

(73) Assignee: University of Rochester, Rochester, NY (US)

( * ) Notice: Subject to any disclaimer, the term of this patent is extended or adjusted under 35 U.S.C. 154(b) by 515 days.

(21) Appl. No.: 15/302,423

(22) PCT Filed: Apr. 7, 2015

(86) PCT No.: PCT/US2015/024783
§ 371 (c)(1),
(2) Date: Oct. 6, 2016

(87) PCT Pub. No.: WO2015/157337
PCT Pub. Date: Oct. 15, 2015

(65) Prior Publication Data
US 2017/0020462 A1 Jan. 26, 2017

Related U.S. Application Data

(60) Provisional application No. 61/977,618, filed on Apr. 9, 2014.

(51) Int. Cl.
*A61B 6/00* (2006.01)
*A61B 5/00* (2006.01)
(Continued)

(52) U.S. Cl.
CPC .............. *A61B 5/7275* (2013.01); *A61B 1/04* (2013.01); *A61B 5/0071* (2013.01);
(Continued)

(58) Field of Classification Search
None
See application file for complete search history.

(56) References Cited

U.S. PATENT DOCUMENTS

| 2005/0140982 A1 | 6/2005 | Chen et al. |
| 2006/0115834 A1* | 6/2006 | Racila ................ C12Q 1/6886 435/6.14 |

(Continued)

FOREIGN PATENT DOCUMENTS

WO    WO 2010/048281 A1    4/2010

OTHER PUBLICATIONS

Burke et al (second harmonic generation reveals matrix alterations during breast tumor progression).*
(Continued)

*Primary Examiner* — Joel F Brutus
(74) *Attorney, Agent, or Firm* — Patent Technologies, LLC; Robert D. Gunderman, Jr.

(57) ABSTRACT

A method and apparatus for determining the progressive potential of a disease is disclosed. The forward to backward propagating second harmonic generation signal derived from a second harmonic generation instrument is used to assess the collagen microstructure of imaged body tissue by way of numerical values that are in turn used to determine the progressive or metastatic potential of the disease. The disease may, for example, be a cancer such as breast cancer,
(Continued)

lung fibrosis, colorectal adenocarcinoma, or the like. The apparatus may include in vivo instruments or laboratory diagnostic instruments with methods disclosed herein.

18 Claims, 7 Drawing Sheets

(51) Int. Cl.
    *G02F 1/37*     (2006.01)
    *G16H 30/40*     (2018.01)
    *G16H 50/30*     (2018.01)
    *A61B 1/04*     (2006.01)
    *G01N 21/63*     (2006.01)
    *G01N 21/64*     (2006.01)

(52) U.S. Cl.
    CPC .......... *A61B 5/0075* (2013.01); *A61B 5/0084* (2013.01); *A61B 5/4842* (2013.01); *A61B 5/4887* (2013.01); *G02F 1/37* (2013.01); *G16H 30/40* (2018.01); *G16H 50/30* (2018.01); *G01N 21/636* (2013.01); *G01N 21/6486* (2013.01)

(56) References Cited

U.S. PATENT DOCUMENTS

| | | | |
|---|---|---|---|
| 2008/0015448 A1* | 1/2008 | Keely | A61B 5/0091 600/477 |
| 2009/0084980 A1 | 4/2009 | Mertz | |
| 2013/0057873 A1* | 3/2013 | Brown, III | A61B 5/0059 356/517 |
| 2013/0287688 A1* | 10/2013 | Jain | A61K 31/4178 424/9.1 |

OTHER PUBLICATIONS

Albain et al (Prognostic and predictive value of the 21-gene recurrence score assay in postmenopausal women with node positive, oestrogen-receptor-positive breast cancer on chemotherapy: a retrospective analysis of a randomised trial).*

Hall et al (Simultaneous determination of the second-harmonic generation emission directionality and reduced scattewring coefficient from three-dimensiona; imaging of thick tissues).*

* cited by examiner

METHOD AND APPARATUS TO DIAGNOSE THE METASTATIC OR PROGRESSIVE POTENTIAL OF CANCER, FIBROSIS AND OTHER DISEASES

CROSS REFERENCE TO RELATED PATENT APPLICATIONS

This application claims priority to U.S. Patent Application Ser. No. 61/977,618 filed Apr. 9, 2014 entitled "Method And Apparatus To Diagnose Metastatic And Progressive Potential Of Cancer, Fibrosis, And Other Diseases" by Perry, Brown, Burke, Kottmann, Sime and Sharp, and to international Application Number PCT/US15/24783 filed Apr. 7, 2015, the entire disclosures of which are incorporated herein by reference in their entirety.

STATEMENT REGARDING FEDERALLY SPONSORED RESEARCH OR DEVELOPMENT

This invention was made with government support under contract number W81 XWH-09-1-0405 awarded by the Department of Defense. The government has certain rights in the invention.

BACKGROUND OF THE INVENTION

1. Field of the Invention

The present invention relates generally to the field of pathology, and, more particularly, to a method and apparatus to diagnose the metastatic or progressive potential of cancer, fibrosis and other diseases.

2. Description of Related Art

Determining the potential for cancer to metastasize or other diseases such as lung fibrosis to progress and become fatal has profound implications in patient treatment as well as the development of new therapies and treatments. Predicting how a disease will progress given various or no treatment options is of tremendous value to the practitioner, the patient, and also to the medical research community. Unfortunately, the various diagnostic tools available today do not provide predictions with a sufficient degree of confidence, and as such, over treatment or non-targeted treatment is common. With treatments such as chemotherapy, this approach has profound health implications for the patient, both physical and mental. What is needed is a method and apparatus to diagnose the metastatic or progressive potential of various diseases such as cancer, fibrosis, and the like.

BRIEF SUMMARY OF THE INVENTION

In accordance with the present invention, there is provided a method for determining the progressive potential of a disease, the method comprising the steps of imaging body tissue using a second harmonic generation instrument; determining the ratio of the forward to backward propagating second harmonic generation signal derived from the imaging of the body tissue with the second harmonic generation instrument; assessing the collagen microstructure of the imaged body tissue using the ratio of the forward to backward propagating second harmonic generation signal; comparing the ratio of the forward to backward propagating second harmonic generation signal to the ratio of the forward to backward propagating second harmonic generation signal of other tissue samples; and determining the progressive potential of the disease by numerical values derived from the ratio of the forward to backward propagating second harmonic generation signal of the imaged body tissue. The disease may, for example, be lung fibrosis, a cancer such as breast cancer or colorectal adenocarcinoma, or the like.

The foregoing paragraph has been provided by way of introduction, and is not intended to limit the scope of the invention as described by this specification, claims and the attached drawings.

BRIEF DESCRIPTION OF THE DRAWINGS

The invention will be described by reference to the following drawings, in which like numerals refer to like elements, and in which.

Figure 1:
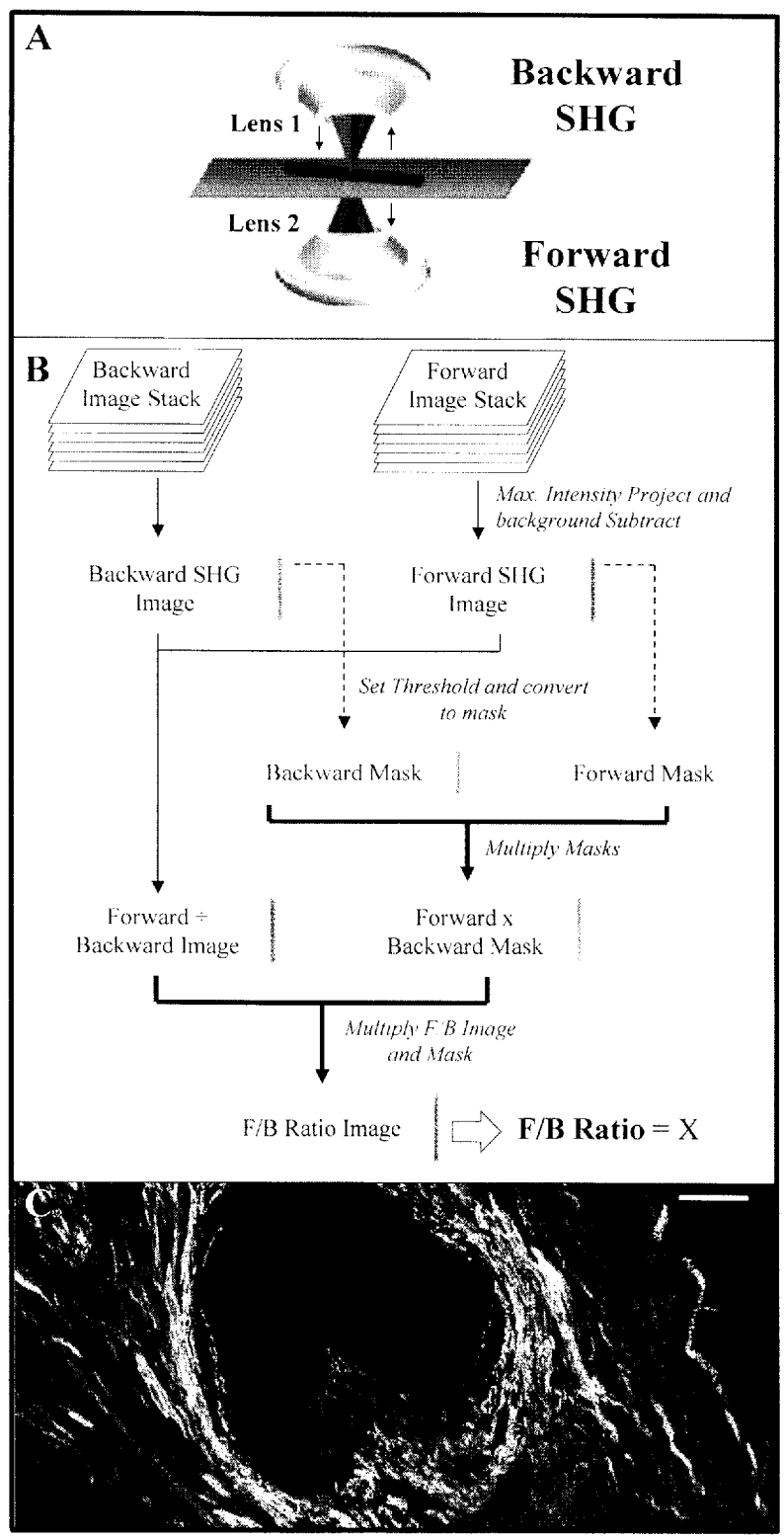
FIG. 1 depicts methodology diagrams for the present invention.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by this specification, claims, and drawings attached hereto.

DESCRIPTION OF THE PREFERRED EMBODIMENTS

A method and apparatus for determining the progressive potential of a disease is described. The method comprises the steps of imaging body tissue using a second harmonic generation instrument; determining the ratio of the forward to backward propagating second harmonic generation signal derived from the imaging of the body tissue with the second harmonic generation instrument; assessing the collagen microstructure of the imaged body tissue using the ratio of the forward to backward propagating second harmonic generation signal; comparing the ratio of the forward to backward propagating second harmonic generation signal to the ratio of the forward to backward propagating second harmonic generation signal of other tissue samples; and determining the progressive potential of the disease by numerical values derived from the ratio of the forward to backward propagating second harmonic generation signal of the imaged body tissue. The disease may, for example, be lung fibrosis, a cancer such as breast cancer or colorectal adenocarcinoma, or the like.

An apparatus employing this method may be embodied in an endoscope arrangement, for example. Such an apparatus is further described herein.

By way of example, and not limitation, the specific use of the method and apparatus of the present invention is further described using two examples—using second harmonic generation to predict patient outcome in solid tumors and the prediction of fatal lung fibrosis. After reading this specification, one can appreciate and understand the applicability of the present invention to other diseases in addition to the examples provided herewith.

Example 1

Using Second Harmonic Generation to Predict Patient Outcome in Solid Tumors

Introduction:

Over-treatment of estrogen receptor positive (ER+), lymph node-negative (LNN) breast cancer patients with chemotherapy is a pressing clinical problem that can be addressed by improving techniques to predict tumor metastatic potential. Here we demonstrate that second harmonic generation (S-HG) analysis of primary tumor biopsies can provide prognostic information about the metastatic outcome of ER+, LNN breast cancer, as well as stage I colorectal adenocarcinoma.

Methods:

SHG is an optical signal produced by fibrillar collagen. The ratio of the forward-to-backward emitted SHG signals (F/B) is sensitive to changes in structure of individual collagen fibers. F/B from excised primary tumor tissue was measured in a retrospective study of LNN breast cancer patients who had received no adjuvant systemic therapy and related to metastasis-free survival (MFS) and overall survival (OS) rates. In addition. F/B was studied for its association with the length of progression-free survival (PFS) in a subgroup of ER+ patients who received tamoxifen as first-line treatment for recurrent disease, and for its relation with OS in stage I colorectal and stage I lung adenocarcinoma patients.

Results:

In ER+, but not in ER-negative (ER-), LNN breast cancer patients an increased natural log of the F/B was significantly associated with a favorable MFS and OS. On the other hand, an increased natural log of the F/B was associated with shorter PFS in ER+recurrent breast cancer patients treated with tamoxifen. In stage I colorectal adenocarcinoma, an increased F/B was significantly related to poor OS, however this relationship was not statistically significant in stage I lung adenocarcinoma; and further testing is required.

Conclusion:

Within ER+, LNN breast cancer specimens F/B can stratify patients based upon their potential for tumor aggressiveness. This offers a "matrix-focused" method to predict metastatic outcome that is complementary to genomic "cell-focused" methods. This may contribute to improved metastatic prediction, and hence may help to reduce patient over-treatment.

Introduction

Breast cancer is the leading cause of cancer related mortality in women (American Cancer Society. Cancer Facts & Figures 2012. Atlanta: American Cancer Society: 2012), predominantly due to metastasis (Fisher E R, Gregorio R M, Fisher B, Redmond C. Vellios F, Sommers S C: The pathology of invasive breast cancer. A syllabus derived from findings of the National Surgical Adjuvant Breast Project (protocol no. 4). *Cancer* 1975, 36(1): 1-85). After surgical resection of the primary tumor, the clinician must choose adjuvant therapy based upon the metastatic potential. Due to their aggressive biological behavior, ER-negative (ER-) tumors are treated with chemotherapy in the majority of patients. However, in ER+ patients whose cancer has not yet spread to the lymph nodes (LNN), the choice between hormonal therapy alone, or in combination with chemotherapy, is more uncertain. Following current standard of care, it is estimated that 40% of these patients will be "over-treated", receiving chemotherapy even though they would not go on to develop metastatic disease, causing many to endure the emotional distress and severe side effects accompanying chemotherapy (Weigelt B, Peterse J L, van't Veer L J: Breast cancer metastasis: markers and models. *Nature reviews Cancer* 2005, 5(8):591-602). As such, there is a pressing clinical need to accurately predict which ER+. LNN patients have a lower metastatic potential and thus can be spared from over-treatment.

Metastatic potential and treatment response can be predicted to varying degrees of accuracy using traditional histopathology, gene expression measurements (Paik S, Shak S, Tang G, Kim C, Baker J. Cronin M, Baehner F L, Walker M G, Watson D, Park T et al: A multigene assay to predict recurrence of tamoxifen-treated, node-negative breast cancer. *The New England journal of medicine* 2004, 351(27):2817-2826. Wang Y, Klijn J G. Zhang Y, Sieuwerts A M, Look M P. Yang F. Talantov D, Timmermans M, Meijer-van Gelder M E. Yu J et al: Gene-expression profiles to predict distant metastasis of lymph-node-negative primary breast cancer. *Lancet* 2005, 365(9460):671-679, van't Veer L J, Dai H, van de Vijver M J, He Y D, Hart A A, Mao M, Peterse H L, van der Kooy K, Marton M J, Witteveen A T et al: Gene expression profiling predicts clinical outcome of breast cancer. *Nature* 2002. 415(6871):530-536. Parker J S, Mullins M, Cheang M C, Leung S, Voduc D, Vickery T. Davies S, Fauron C, He X. Hu Z et al: Supervised risk predictor of breast cancer based on intrinsic subtypes. *Journal of clinical oncology: official journal of the American Society of Clinical Oncology* 2009, 27(8):1160-1167. Filipits M, Rudas M, Jakesz R. Dubsky P, Fitzal F. Singer C F, Dietz O, Greil R, Jelen A. Sevelda P et al: A new molecular predictor of distant recurrence in ER-positive, HER2-negative breast cancer adds independent information to conventional clinical risk factors. *Clinical cancer research: an official journal of the American Association for Cancer Research* 2011, 17(18):6012-6020), immunohistochemistry of gene related protein products (Ring B Z, Seitz R S, Beck R, Shasteen W J, Tarr S M, Cheang M C, Yoder B J, Budd G T, Nielsen T O, Hicks D G et al: Novel prognostic immunobistochemical biomarker panel for estrogen receptor-positive breast cancer. *Journal of clinical oncology: official journal of the American Society of Clinical Oncoloy* 2006, 24(19):3039-3047.

Philippar U, Roussos E T. Oser M, Yamaguchi H, Kim H D, Giampieri S. Wang Y. Goswami S, Wyckoff J B. Lauffenburger D A et al: A Mena invasion isoform potentiates EGF-induced carcinoma cell invasion and metastasis. *Developmental cell* 2008, 15(6):813-828), mass-spectrometry based protein levels (Liu N Q, Stingi C, Look M P, Smid M, Braakman R B, De Marchi T, Sieuwerts A M, Span P N, Sweep F C, Linderholm B K et al: Comparative proteome analysis revealing an 11-protein signature for aggressive triple-negative breast cancer. *Journal of the National Cancer*

*Institute* 2014, 106(2):djt376), image analysis of cell-stromal interactions within the tumor (Robinson B D, Sica G L, Liu Y F, Rohan T E, Gertler F B, Condeelis J S, Jones J G: Tumor microenvironment of metastasis in human breast carcinoma: a potential prognostic marker linked to hematogenous dissemination. *Clinical cancer research: an official journal of the American Association for Cancer Research* 2009, 15(7):2433-2441), and various other techniques. These techniques provide insights into neoplastic cell function, however, implicit in Steven Paget's "Seed and Soil" hypothesis is the idea that metastasis involves interactions between tumor cells and their microenvironment (Paget S: The Distribution of Secondary Growths in Cancer of the Breast. The Lancer 1889, 133(3421):571-573). Therefore, we have explored the possibility that the tumor extracellular matrix, specifically collagen structure quantified with second harmonic generation microscopy, may provide additional information on tumor metastatic ability.

SHG is an intrinsic optical signal in which two incoming photons scatter off of material, producing one emission photon of half the incoming wavelength (FIG. 1). In tumors, SHG is generated by fibrillar collagen and is sensitive to the microscopic structure of the scattering material. Hence SHG emission directionality is sensitive to the diameter of the fibrils that are bundled into collagen fibers, as well as their spacing within the fiber, and the disorder in their packing (Han X. Burke R M, Zettel M L, Tang P. Brown E B: Second harmonic properties of tumor collagen: determining the structural relationship between reactive stroma and healthy stroma. *Optics express* 2008, 16(3):1846-1859. Lacomb R, Nadiarnykh O, Townsend S S, Campagnola P J: Phase Matching considerations in Second Harmonic Generation from tissues: Effects on emission directionality, conversion efficiency and observed morphology. *Optics communications* 2008, 281(7):1823-1832. Williams R M, Zipfel W R, Webb W W: Interpreting second-harmonic generation images of collagen I fibrils. *Biophysical journal* 2005, 88(2):1377-1386). The ratio of the forward-emitted to backward-emitted SHG (where "forward" is the direction of the incident excitation laser) is known as the F/B ratio and is sensitive to these structural properties of collagen fibers (FIG. 1). We have shown that the average F/B of patient biopsy samples can differentiate healthy and breast tumor tissue, and changes with tumor grade and stage (Perry S W, Schueckler J M, Burke K, Arcuri G L, Brown E B: Stromal matrix metalloprotease-13 knockout alters Collagen I structure at the tumor-host interface and increases lung metastasis of C57BL/6 syngeneic E0771 mammary tumor cells. *BMC cancer* 2013, 13:411). Since SHG is an intrinsic optical signature, measurements of F/B can be performed on typical pathology slides without additional contrast reagents. Furthermore, determination of the average F/B in a sample involves only a straightforward, automated application of pixel intensity analysis that does not require a trained observer. Therefore F/B analysis is an attractive candidate to apply to the prediction of tumor aggressiveness. Here we show that the natural log of the F/B can predict MFS in ER+, LNN breast cancer patients. In a small subset of breast cancer patients treated with tamoxifen in a recurrent setting, the natural log of the F/B is also found to be associated with shorter PFS. We further show that F/B was related to OS in stage I colorectal adenocarcinoma, pointing to the possibility that collagen structure, as reported on by F/B, and tumor metastatic capacity are linked in both tumor types.

Methods

Patient Samples

Three-hundred and forty-four human breast tumor samples were used from a collection at the Erasmus Medical Center (Rotterdam, Netherlands), which were primarily from one breast cancer genetic expression study (Wang Y, Klijn J G, Zhang Y. Sicuwerts A M. Look M P, Yang F, Talantov D, Timmermans M. Meijer-van Gelder M E. Yu J et al: Gene-expression profiles to predict distant metastasis of lymph-node-negative primary breast cancer. *Lancet* 2005, 365(9460):671-679) and later supplemented by 58 additional ER– samples (Yu J X, Sicuwerts A M, Zhang Y, Martens J W, Smid M. Klijn J G, Wang Y, Foekens J A: Pathway analysis of gene signatures predicting metastasis of node-negative primary breast cancer. *BMC cancer* 2007, 7:182). These fresh-frozen tissues were initially processed for microarray analysis, and were at a later stage processed for inclusion on a tissue-microarray (TMA) in cases where formalin-fixed paraffin embedded tissues were available as well. Initial sample acquisition was approved by the medical ethics committee (number 02•953) and conducted in accordance with the code of conduct of Federation of Medical Scientific Societies in the Netherlands (www.fmwv.nl). All patients were LNN and had not been treated with neoadjuvant nor adjuvant therapy. This allowed for the study of the natural course of the disease and pure tumor aggressiveness, without potentially being confounded by systemic therapy. Some patients received radiation therapy, which has been shown not to affect distant metastases (Effects of Radiotherapy and Surgery in Early Breast Cancer—An Overview of the Randomized Trials. *New England Journal of Medicine* 1995, 333(22):1444-1456), our main focus of this study. The median patient age was 52 years. Follow-up data was recorded every 3 months for 2 years, every 6 months for years 3-5, and every 12 months afterwards. All samples were collected in triplicate as 5 µm thick, 0.5 mm diameter core tissue samples and mounted as TMA slides, in which the uniform tumor presence was verified by hematoxylin and eosin (H&E) staining. Note that the presence of H&E staining does not affect the reported F/B (Lacomb R. Nadiarnykh O, Townsend S S, Campagnola P J: Phase Matching considerations in Second Harmonic Generation from tissues: Effects on emission directionality, conversion efficiency and observed morphology. *Optics communications* 2008, 281(7):1823-1832). Patients were tested for ER and progesterone receptor (PgR) status using immunohistochemistry, where the cutoff for receptor positivity was 10% positive tumor cells. Bloom and Richardson grade and HER2 status data were assessed as described (Liu N Q. De Marchi T, Timmernmans A M. Beekhof R, Trapman-Jansen A M, Foekens R, Look M P, van Deurzen C H, Span P N, Sweep F C et al: Ferritin heavy chain in triple negative breast cancer: a favorable prognostic marker that relates to a cluster of differentiation 8 positive (CD8+) effector T-cell response. *Molecular & cellular proteomics: MCP* 2014, 13(7):1814-1827) and were available as well for the tissues included in the TMA. In total, 221 TMA-cases were eligible for analysis of F/B ratio, of which 125 were ER+ and 96 were ER–.

Stage I colorectal adenocarcinoma samples were purchased from the Yale tissue pathology (YTMA-8, New Haven Conn.). Samples were processed as TMA with one 5 µm thick, 0.5 mm diameter sample per patient, unstained, from within the primary tumor. Samples were collected from 1970-1982 with up to 31 years of follow-up data, resulting in a total of 69 stage I primary colorectal tumors. Lung adenocarcinoma samples were acquired at the University of Michigan, providing a total of 55 stage I lung adenocarcinoma cases (Beer D O, Kardia S L R, Iluang C-C, Giordano T J, Levin A M. Misek D E, Lin L, Chen O, Gharib T O, Thomas D O et al: Gene-expression profiles predict survival of patients with lung adenocarcinoma. *Nature medicine* 2002, 8(8):816-824). Tissue was collected between 1994-2000 with the consent of the patient and approval from the local Institutional Review Board. All patients underwent the same treatment, surgical resection with intra-thoracic nodal sampling. The lung adenocarcinoma samples were provided as a 5 µm thick section through the full diameter of the tissue. Analysis of H&E stained samples by a trained clinical pathologist was used to ensure images were taken within the tumor proper.

Imaging

The method for determining F/f of a thin tissue sample has been previously described [17]. Briefly, SHG imaging was performed on an Olympus BX61WI upright microscope. A Spectra Physics MaiTai Ti:Sapphire laser (circularly polarized, 810 nm, 100 fs pulses at 80 MHz) was directed through an Olympus Fluoview FV300 scanner. This was focused through an Olympus UMPLFL20XW water-immersion lens (20×, 0.95 NA), which subsequently captured backward propagating SHG signal. This SHG signal was separated from the excitation beam using a 670 nm dichroic mirror, filtered using a 405 nm filter (HQ405/30m-2P, Chroma, Rockingham, Vt.), and collected by a photomultiplier tube (Hamamatsu HC125-02). The forward scattered SHG was collected through an Olympus 0.9 NA condenser, reflected by a 565 nm dichroic mirror (565 DCSX. Chroma, Rockingham, Vt.) to remove excitation light, filtered by a 405 nm filter (HQ405/30m-2P, Chroma, Rockingham, Vt.) and captured by photomultiplier tube (Hamamatsu HC125-02). During acquisition of the daily calibration sample, a dilute fluorescein isothiocyanate (FITC) solution, a 535/40 filter (535/40m-2P, Chroma, Rockingham, Vt.) replaced the 405 nm filters. Forward- and backward-scattered SHG images were simultaneously collected as a stack of 11 images spaced 3 m apart, with a 660 µm field of view. Imaging conducted on TMA slides of H&E stained, 0.5 mm diameter breast cancer and colon cancer samples permitted one image stack at the center of each sample. For the larger (approximately 3 cm wide) lung cancer samples, 3 locations were chosen randomly in each sample and the 3 resultant F/B values (see below) were averaged.

Image Analysis image analysis was conducted with ImageJ (Schneider C A, Rasband W S, Eliceiri K W: NIH Image to ImageJ: 25 years of image analysis. *Nature methods* 2012, 9(7):671-675). Tissue sections were 5 µm thick, comparable to the axial resolution of the SHG images, hence there was effectively a single layer of collagen in each sample. "autofocused" with a maximum intensity projection of both the forward and backward image stacks. This produced a single image pair (forward scattered SHG "F", and backwards scattered SHG "B") for each imaged location. A maximum intensity projection of an 11 image scan taken with a closed microscope shutter was used to determine the background noise of the imaging system, which was then subtracted from each image. A common threshold (40 out of a maximum possible pixel count of 4095 a.u.) was initially determined by a blinded observer viewing ~30 image pairs and choosing the threshold that best distinguished pixels within fibers from those in the background. This single threshold was applied to each image to identify pixels within fibers by creating a pair of masks (one for F, one for B), in which all of the pixels above threshold were set to 1, and all of the pixels below threshold were set to zero. These masks were multiplied to create one "forward×backward mask" whose pixels were equal to 1 only when they were equal to 1 in both the forward and backward masks. The background subtracted F and B images were divided to produce an F/B image of the sample, which was multiplied by the "forward× backward mask", and the average value of all nonzero pixels yielded the sample's average F/B (FIG. 1).

Day-to-day variations in optical alignments were normalized by imaging a standard solution of FITC daily and applying a normalization factor for each detector pathway that rendered the signal from the standard FITC sample constant over time.

Statistics

STATA, release 13 (StataCorp, Texas, USA) and Prism 5 software (CiraphPad, La Jolla, Calif.) was used for statistical analysis. MFS was defined as the date of confirmation of a distant metastasis after symptoms reported by the patient, detection of clinical signs, or at regular follow-up. OS was defined as time until death, any cause, while patients who died without evidence of disease were censored at their last follow-up time.

PFS was defined as the time from start of tamoxifen treatment until a second line of treatment was needed, or until death. The relationship between the natural log of the F/B and survival rate was assessed using the Kaplan-Meier method and evaluated using the log-rank test for trend. Multivariate Cox proportional hazard analysis was applied to evaluate the prognostic value of the natural log of the F/B, age, menopausal status, tumor size, tumor grade, ER. PgR and HER2 status. Differences were considered statistically significant when the 2-sided p-value was below 0.05.

Results

F/B and Relationship with Patient and Tumor Characteristics

The median natural log of the F/B of and interquartile range in all tumors was 2.228 (0.416) (Table 1). The natural log of the F/B was not significantly associated with the age or menopausal status of the patient. There were also no significant correlations with tumor size, tumor grade, and HER2 status. In contrast, compared with steroid hormone-positive tumors, F/B was higher in ER− (p<0.001) and PgR-negative tumors (p=0.003), respectively (Table 1).

Metastasis-Free Survival in Breast Cancer Patients

Univariate analysis of the natural log of the primary tumor F/B showed no statistically significant relationship between F/B and the length of MFS (Hazard Ratio, HR=0.706; 95% confidence interval, CI 0.351-1.422: p=0.330) within the combined (ER+ and ER−) sample set. Because mechanisms of breast tumor progression varies based on ER status, and because ER+ and ER− tumors are biologically very different tumors (Gruvberger S, Ringner M, Chen Y, Panavally S, Saal L H, Borg A, Ferno M, Peterson C, Meltzer P S: Estrogen receptor status in breast cancer is associated with remarkably distinct gene expression patterns. *Cancer research* 2001, 61(16):5979-5984. Anderson W F, Chu K C, Chatterjee N, Brawley O, Brinton L A: Tumor variants by hormone receptor expression in white patients with node-negative breast cancer from the surveillance, epidemiology, and end results database. *Journal of clinical oncology: official journal of the American Society of Clinical Oncology* 2001, 19(1):18-27), we then analyzed the prognostic value of F/B status in ER subgroups separately. Within the ER+ subgroup, in Cox regression analysis using F/B as a continuous variable there was a statistically significant relationship between the natural log of the primary tumor F/B and MFS (HR=0.23; 95% CI 0.08-0.65; p=0.005) (Table 2), but within the ER− population the relationship was not statistically significant (HR=2.72; 95% CI 0.8104-9.173; p=0.105). The ER+, LNN patient samples were then divided into four equal quarters consisting of a high natural log of the F/B (above 2.354: Q4), a low natural log of the F/B (below 1.954: Q1), and 2 mid-range F/B categories (range 1.954-2.168: Q2, and 2.168-2.354: Q3), and plotted in a Kaplan Meier curve (FIG. 2a). Patients with tumors with low F/B (Q1) showed the worst MFS, while those with high F/B (Q4) showed the best MFS. The 2-mid range categories (Q2 and Q3) showed an intermediate MFS (logrank trend p=0.004). In Cox multivariate regression analysis for MFS in ER+ patients, corrected for the traditional prognostic factors age, menopausal status of the patient, tumor size, tumor grade. PgR, and HER2 status, an increasing natural log of the F/B was significantly associated with longer MFS (HR=0.16; 95% CI 0.05-0.55; p=0.004) (Table 2).

Overall Survival in Breast Cancer Patients

Next we tested whether F/B of the primary tumor was also significantly related to OS in the ER+, LNN group of patients. Univariate Cox regression analysis showed that the natural log of primary tumor F/B was borderline statistically significantly related to OS (HR=0.34; 95% CI 0.11-1.03; p=0.057). A logrank test for trend analysis of Kaplan Meier curves with F/B divided into Q1-Q4 shows a significant relationship between increasing natural log of the primary tumor F/B and longer OS (FIG. 2b, p=0.03). A multivariate Cox analysis of this data showed that the natural log of the F/B ratio, when corrected for traditional prognostic factors, was borderline significantly related to OS (HR=0.28; 95% CI 0.07-1.10; p=0.068) (Table 3).

Tamoxifen Treatment

Figure 3:
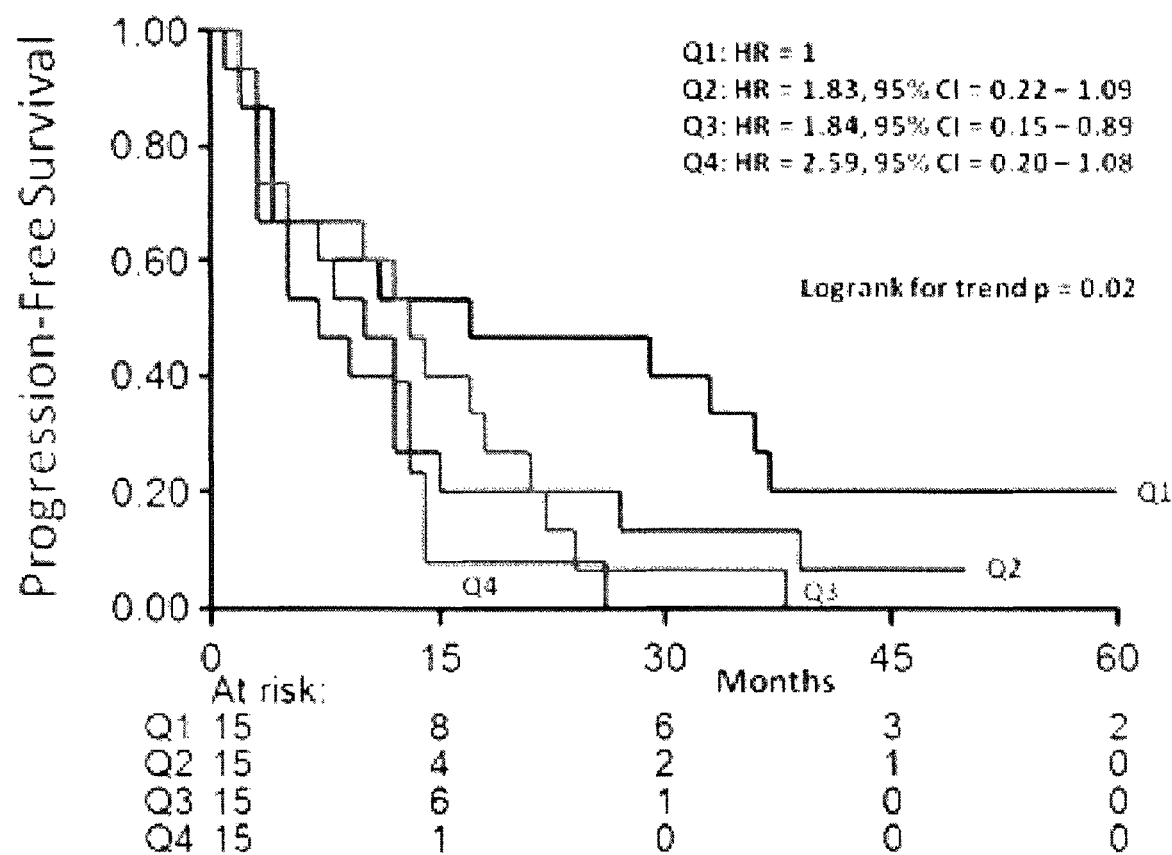
FIG. 3 is a graph depicting progression free survival as a function of FIB in ER+ recurrent breast cancer patients treated with tamoxifen.

The previous studies were conducted in untreated patients in order to analyze the relationship between F/B of the primary tumor and tumor aggressiveness and pure prognosis. A subset of these patients did metastasize to a distant site and were then treated with tamoxifen as first-line monotherapy. Therefore we evaluated this subset of ER+ breast cancer patients to determine whether F/B of the primary tumor was significantly related to PFS after start of therapy for recurrent disease. The hazard ratio of the natural log of the natural log of the primary tumor F/B was 3.39 (95% CI 1.22-9.37; p=0.019) and the logrank test for trend analysis of Kaplan Meier curves in equal quarters showed a significant relationship (p=0.02) between primary tumor F/B and PFS (FIG. 3). Interestingly, the trend in PFS (i.e. lower primary tumor FIB was associated with slower disease progression) was found to be the opposite of that observed in MFS and OS in the untreated ER+ patients (i.e. lower primary tumor F/B was associated with shorter MFS and OS times).

Overall Survival as a Function of F/B in Other Solid Tumor Types

Based on the significant relationships revealed in the breast cancer samples, we investigated colorectal and lung adenocarcinoma, other solid tumor types in which tumor cell/matrix interactions may significantly affect metastasis. Similar to ER+, LNN breast cancer patients, stage I colorectal and lung adenocarcinoma are a subset of patients where there is a clinical need to assist the physician in deciding the appropriate level of treatment for the patient. In stage I colorectal adenocarcinoma there was a significant relationship between the F/B of the primary tumor and patient OS (FIG. 4a). Notably, the observed trend (i.e. a lower F/B was associated with longer OS) was the opposite of the trend observed in the untreated ER+, LNN breast cancer samples, suggesting a different mechanistic relationship between metastasis and collagen fiber microstructure. In contrast, stage I lung adenocarcinoma showed no significant relationship between the F/B of the primary tumor and OS (FIG. 4b). This suggests that not all solid tumors undergoing metastasis elicit identical collagen restructuring or utilize identical mechanisms relating metastatic ability and collagen microstructure. Identification of these mechanisms through experimentation is important in order to apply the methods of the present invention to other solid tumors.

Currently the ER+, LNN breast cancer population suffers from over-treatment as many patients receive chemotherapy even though metastatic disease never would have arisen. As such, there is a pressing need to improve clinicians' ability to predict which tumors are likely to metastasize in this population. Current methods to predict metastasis are "cell focused", using quantification of gene and protein expression levels, or cellular morphology and cell-cell interactions (Parker J S, Mullins M, Cheang M C, Leung S, Voduc D, Vickery T, Davies S, Fauron C. He X, Hu Z et al: Supervised risk predictor of breast cancer based on intrinsic subtypes. *Journal of clinical oncology: official journal of the American Society of Clinical Oncology* 2009, 27(8):1160-1167. Filipits M. Rudas M, Jakesz R. Dubsky P, Fitzal F, Singer C F, Dietze O, Greil R, Jelen A, Sevelda P et al: A new molecular predictor of distant recurrence in ER-positive, HER2-negative breast cancer adds independent information to conventional clinical risk factors. *Clinical cancer research: an official journal of the American Association for Cancer Research* 2011, 17(18):6012-6020. Ring B Z, Seitz R S, Beck R, Shasteen W J, Tarr S M, Cheang M C, Yoder B J, Budd O T, Nielsen T O, Hicks D G et al: Novel prognostic immunohistochemical biomarker panel for estrogen receptor-positive breast cancer. *Journal of clinical oncology: official journal of the American Society of Clinical Oncology* 2006, 24(19):3039-3047. Liu N Q, Stingl C, Look M P, Smid M, Braakman R B, De Marchi T, Sieuwerts A M, Span P N, Sweep F C, Linderholm B K et al: Comparative proteome analysis revealing an 11-protein signature for aggressive triple-negative breast cancer. *Journal of the National Cancer Institute* 2014, 106(2):djt376). However, the process of metastasis is a complex interplay between tumor cells and their microenvironment, including the extracellular matrix (Helleman J. Jansen M P, Ruigrok-Ritstier K, van Staveren I L, Look M P, Meijer-van (elder M E, Sieuwerts A M, Klijn J G, Sleijfer S, Foekens J A et al: Association of an extracellular matrix gene cluster with breast cancer prognosis and endocrine therapy response. *Clinical cancer research: an official journal of the American Association for Cancer Research* 2008, 14(17):5555-5564. Joyce J A, Pollard J W: Microenvironmental regulation of metastasis. *Nature reviews Cancer* 2009, 9(4):239-252). Therefore we explored the prognostic ability of a "matrix focused" measurement, the SHG F/B of the primary tumor.

Studies demonstrating that SHG imaging can differentiate healthy and tumor tissue in ovarian (Nadianiykh O, LaComb R B. Brewer M A. Campagnola P J: Alterations of the extracellular matrix in ovarian cancer studied by Second Harmonic Generation imaging microscopy. *BMC cancer* 2010, 10:94), basal cell) Lin S J, Joe S H, Kuo C J, Wu R J, Lin W C, Chen J S. Liao Y H, Hsu C J, Tsai T F, Chen Y F et al: Discrimination of basal cell carcinoma from normal dermal stroma by quantitative multiphoton imaging. *Optics letters* 2006, 31(18):2756-2758), and pulmonary cancers (Wang C C, Li F C, Wu R J, Hovhannisyan V A, Lin W C, Lin S J, So P T, Dong C Y: Differentiation of normal and cancerous lung tissues by multiphoton imaging. *Journal of biomedical optics* 2009, 14(4):044034), establish two useful aspects of SHG: it is an intrinsic signal that does not require additional processing of tissue, and, if used to quantify intensity but not morphology, the analysis is automatable and does not require a trained technician. We recently applied this methodology in breast cancer, demonstrating that the simple intensity-based SHG F/B is significantly different amongst different breast tumor types (Perry S W, Schueckier J M, Burke K, Arcuri G L, Brown E B: Stromal matrix metalloprotease-13 knockout alters Collagen I structure at the tumor-boat Interface and increases lung metastasis of C57BL/6 syngeneic E0771 mammary tumor cells. *BMC cancer* 2013, 13:411). In the current work, we demonstrate that F/B analysis of the primary tumor is a prognostic indicator in the ER+, LNN population. Unlike the ER− or ER+ node-positive patients, in which adjuvant chemotherapy is universally applied, the choice of whether or not to prescribe adjuvant chemotherapy for ER+, LNN patients is not easily apparent. Hence this is a population with a significant over-treatment problem requiring improved prognostic indicators. Our results suggest that SHG F/B from the primary tumor specimen may offer insight into eventual metastatic outcome of the patient and thus may help reduce over-treatment. Currently, predicting the time to metastasis in this population is primarily facilitated by histopathology and by genetic screens. These genetic screens quantify gene expression in cells within the tumor, including both the tumor and stromal cells. The SHO-based method demonstrated here may be highly complementary to those genetic screens, as it derives its information from the structure of the extracellular matrix in the primary tumor, rather than from the tumor cells themselves. SHG imaging has been used previously to predict breast cancer survival times, however these studies focused on analysis of morphological information from collagen images, requiring trained pathologists to score the orientation of collagen fibers in images (Conklin M W, Eickhoff J C, Riching K M. Pehlke C A, Eliceiri K W, Prmvenzano P P, Friedl A, Keely P J: Aligned collagen is a prognostic signature for survival in human breast carcinoma. *The American journal of pathology* 2011, 178(3):1221-1232). Furthermore, the majority of that sample population was lymph node positive, while our study focuses on the LNN population, in which the key decision on adjuvant chemotherapy must be made and for whom the risk of over-treatment is high.

Based on the important role that tamoxifen plays as a treatment in almost all ER+ breast cancer patients, after identifying the significant relationship between the natural log of the F/B and patient outcome in untreated patients, we were interested in exploring the prognostic capability of the F/B to determine the effects of tamoxifen on patients with recurrent tumors. Our results revealed that the F/B as measured on the primary tumor was prognostic of PFS after patients who developed a metastasis at a distant site were treated with tamoxifen. Interestingly, the actual relationship between F/B and outcome displayed a trend that was opposite to that in the MFS and OS findings from untreated ER+ patients: In tamoxifen treated recurrent ER+ patients a high F/B was associated with a faster rate of progression, whereas in untreated ER+ patients a high F/B was associated with improved MFS and OS. Tamoxifen is an ER antagonist, indicating this contrast between tamoxifen treated ER+ tumors and untreated ER+ tumors could be due to the roles of ER in tumor progression. To explain this pattern of relationships between recurrence and F/B in ER+ tamoxifen treated tumors, as opposed to untreated ER+ tumors, we therefore hypothesize that differences in primary tumor collagen microstructure may indicate differences in the mechanism by which tumor cells spread, which has the effect of altering susceptibility to later treatment. In an ER+ primary tumor with a low F/B, cells spread into vasculature and to secondary locations, and upon tamoxifen administration these secondary tumors are effectively treated. In an ER+ primary tumor with a high F/B ratio, tumor cells metastasize via different mechanisms which decrease the tumor cell sensitivity to tamoxifen treatment.

The results demonstrating another significant relationship between F/B of the primary tumor and OS, in stage I colorectal adenocarcinoma, indicate that the mechanisms relating metastasis to collagen microstructure may be similar between breast cancer and other solid tumors. Analyzing collagen structure in colorectal adenocarcinomas may thus aid in predicting the OS rates in patients, consequently helping to determine which patients may be able to avoid over-treatment with chemotherapy in that tumor type as well. The fact that the primary tumor F/B was not predictive of metastasis in stage I lung adenocarcinoma provides support for the idea that multiple mechanisms of tumor metastasis may exist, involving differential interplay between tumor cells and matrix microstructure. These alternative mechanisms could be the result of different levels of fibrous tissue in the tissues of origin, (e.g. collagen density is high in breast and colon but not in lung tissue). In the future it may therefore be beneficial to investigate the relationship between primary tumor F/B and metastatic outcome in other solid tumors that are typically characterized as more fibrous, such as pancreatic cancer.

In summary, we have identified the F/B, a simple and easily automated, intensity-based measurement as an independent prognostic indicator of metastatic outcome in ER+ LNN breast cancer patients. Furthermore, escaped tumor cells with a low F/B at the primary site show a better responsiveness to tamoxifen treatment of the recurrence, indicating a possible mechanism by which collagen structure at the primary site affects sensitivity to treatment. The primary tumor F/B is also prognostic in stage I colon adenocarcinoma, suggesting this assay may be useful in multiple types of solid tumors. By imaging the tumor "soil" this method provides information complementary to that offered by current cell-focused techniques, and therefore in combination with those methods may improve prediction of recurrence and hence reduce over-treatment.

TABLE 1

Log F/B ratio and association with breast cancer patient and tumor characteristics

| Characteristics | No. patients (%) | Median levels (Interquartile range) | P |
|---|---|---|---|
| All patients | 221 (100%) | 2.228 (0.416) | |
| Age (years) | | | 0.773* |
| ≤40 | 33 (14.9%) | 2.160 (0.566) | |
| 41-55 | 94 (42.5%) | 2.215 (0.410) | |
| 56-70 | 70 (31.7%) | 2.291 (0.456) | |
| >70 | 24 (10.9%) | 2.198 (0.327) | |
| Menopausal status | | | 0.497† |
| Premenopausal | 113 (51.1%) | 2.200 (0.447) | |
| Postmenopausal | 108 (48.9%) | 2.250 (0.379) | |
| Tumor size | | | 0.188* |
| pT1 (≤2 cm) | 109 (49.3%) | 2.239 (0.356) | |
| pT2 (2-5 cm) | 105 (47.5%) | 2.237 (0.505) | |
| pT3/pT4 (>5 cm) | 7 (3.2%) | 1.830 (0.614) | |
| Tumor grade‡ | | | 0.700* |
| I | 37 (16.7%) | 2.207 (0.288) | |
| II | 77 (34.8%) | 2.233 (0.366) | |
| III | 101 (45.7%) | 2.264 (0.491) | |

TABLE 1-continued

Log F/B ratio and association with breast cancer patient and tumor characteristics

| Characteristics | No. patients (%) | Median levels (Interquartile range) | P |
|---|---|---|---|
| ER status | | | <0.001† |
| Positive | 125 (56.6%) | 2.168 (0.407) | |
| Negative | 96 (43.4%) | 2.311 (0.452) | |
| PgR status | | | 0.003† |
| Positive | 104 (47.1%) | 2.159 (0.392) | |
| Negative | 117 (52.9%) | 2.302 (0.425) | |
| HER2 status | | | 0.121† |
| Positive | 26 (11.8%) | 2.299 (0.399) | |
| Negative | 195 (88.2%) | 2.215 (0.432) | |

*Kruskal-Wallis test
†Two-sample Wilcoxon rank-sum (Mann-Whitney) test
‡Scarff-Bloom-Richardson grade (6 missing values)

TABLE 2

Cox univariate and multivariate regression analysis for MFS in 125 ER+ patients

| | Univariate analysis | | | Multivariate analysis* | | |
|---|---|---|---|---|---|---|
| Variable | HR | 95% CI | p | HR | 95% CI | p |
| Age | | | | | | |
| 41-55 vs 40 years | 0.59 | 0.27-1.32 | 0.203 | 0.80 | 0.35-1.84 | 0.599 |
| 56-70 vs 40 years | 0.56 | 0.25-1.26 | 0.159 | 0.41 | 0.13-1.34 | 0.140 |
| >70 vs 40 years | 0.46 | 0.15-1.36 | 0.159 | 0.32 | 0.08-1.27 | 0.105 |
| Menopausal status | | | | | | |
| Post-vs premenopausal | 0.98 | 0.55-1.73 | 0.938 | 2.46 | 0.89-6.84 | 0.083 |
| Tumor size | | | | | | |
| 2-5 vs ≤2 cm | 1.76 | 0.98-3.14 | 0.056 | 0.85 | 0.43-1.70 | 0.650 |
| >5 vs ≤2 cm | 1.51 | 0.36-6.38 | 0.579 | 0.50 | 0.10-2.42 | 0.386 |
| Tumor grade | | | | | | |
| II vs I | 3.15 | 1.30-7.61 | 0.011 | 2.76 | 1.10-6.92 | 0.030 |
| III vs I | 4.38 | 1.68-11.45 | 0.003 | 3.38 | 1.15-9.93 | 0.027 |
| PgR status | | | | | | |
| Positive vs negative | 0.71 | 0.38-1.85 | 0.297 | 0.61 | 0.30-1.24 | 0.170 |
| HER2 status | | | | | | |
| Positive vs negative | 4.06 | 1.71-9.65 | 0.002 | 3.67 | 1.10-6.92 | 0.009 |
| Log of F/B ratio | 0.23 | 0.08-0.65 | 0.005 | 0.16 | 0.05-0.55 | 0.004 |

*The multivariate model included 123 patients due to 2 missing values for tumor grade.

TABLE 3

Cox univariate and multivariate regression analysis for OS in 125 ER+ patients

| | Univariate analysis | | | Multivariate analysis* | | |
|---|---|---|---|---|---|---|
| Variable | HR | 95% CI | p | HR | 95% CI | p |
| Age | | | | | | |
| 41-55 vs 40 years | 0.49 | 0.21-1.17 | 0.108 | 0.61 | 0.25-1.52 | 0.289 |
| 56-70 vs 40 years | 0.57 | 0.24-1.35 | 0.204 | 0.29 | 0.09-0.95 | 0.041 |
| >70 vs 40 years | 0.33 | 0.09-1.26 | 0.105 | 0.20 | 0.04-0.95 | 0.043 |
| Menopausal status | | | | | | |
| Post-vs premenopausal | 1.14 | 0.61-2.11 | 0.686 | 2.90 | 0.99-8.49 | 0.052 |

TABLE 3-continued

Cox univariate and multivariate regression analysis for OS in 125 ER+ patients

| | Univariate analysis | | | Multivariate analysis* | | |
|---|---|---|---|---|---|---|
| Variable | HR | 95% CI | p | HR | 95% CI | p |
| Tumor size | | | | | | |
| 2-5 vs ≤2 cm | 1.25 | 0.66-2.37 | 0.494 | 0.56 | 0.26-1.20 | 0.137 |
| >5 vs ≤2 cm | 1.66 | 0.39-7.11 | 0.492 | 0.75 | 0.15-3.72 | 0.720 |
| Tumor grade | | | | | | |
| II vs I | 2.53 | 1.02-6.24 | 0.044 | 2.16 | 0.84-5.55 | 0.111 |
| III vs I | 5.02 | 1.89-13.36 | 0.001 | 4.88 | 1.64-14.56 | 0.004 |
| PgR status | | | | | | |
| Positive vs negative | 0.51 | 0.26-1.01 | 0.055 | 0.48 | 0.23-1.01 | 0.054 |
| HER2 status | | | | | | |
| Positive vs negative | 3.15 | 1.11-8.96 | 0.031 | 3.80 | 1.18-12.20 | 0.025 |
| Log of F/B ratio | 0.34 | 0.11-1.03 | 0.005 | 0.29 | 0.07-1.10 | 0.068 |

*The multivariate model included 123 patients due to 2 missing values for tumor grade.

FIG. 1 depicts methodology diagrams, where A, is a depiction of the forward- and backward-propagating SHG signal. Red excitation light is focused into the sample by objective lens 1, then SHG is emitted in the backwards direction (towards lens 1) or the forward direction (towards lens 2). B. A flowchart of the methodology used to analyze SHG images and calculate the F/B ratio. C. An F/B image of one patient sample. Scale bar is 50 microns.

Figure 2:
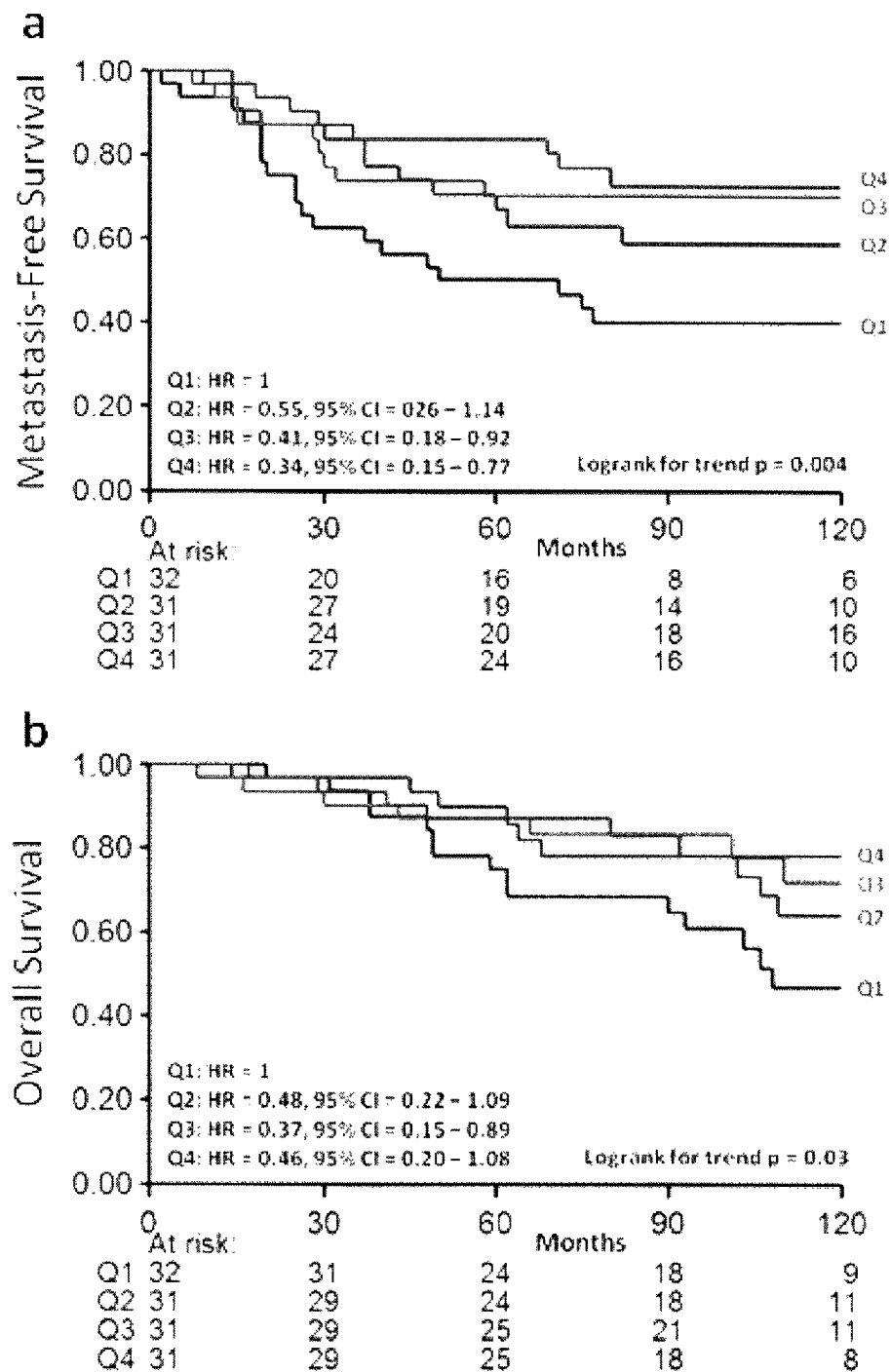
FIG. 2 is a graph depicting metastasis free and overall survival as a function of F/B in ER+, LNN breast cancer.

FIG. 2 depicts Metastasis-free (a) and overall survival (b) as a function of F/B in ER+, LNN breast cancer. The patients are divided in four equal quarters (Q1-Q4) based on their F/B tumor level. Patients at risk at various time points are indicated.

FIG. 3 depicts progression-free survival as a function of F/B in ER+ recurrent breast cancer patients treated with tamoxifen. The patients are divided in four equal quarters (Q1-Q4) based on their F/B tumor level. Patients at risk at various time points are indicated.

Figure 4:
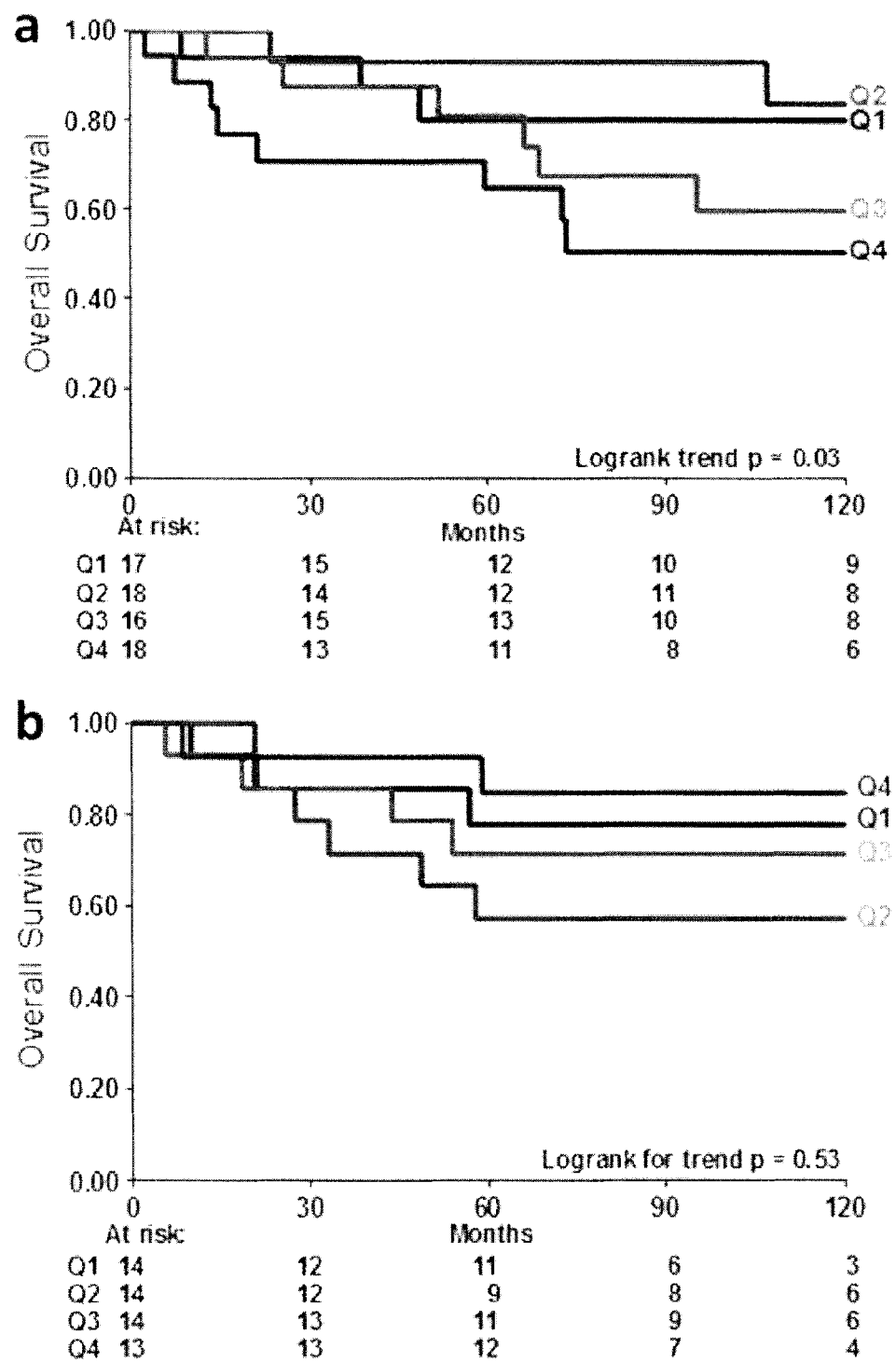
FIG. 4 depicts overall survival of additional solid tumors (a: Stage I Colorectal Adenocarcinoma and b: Stage I Lung Adenocarcinoma) as a function of F/B ratio.

FIG. 4 depicts overall survival of additional solid tumors as a function of F/B ratio. Overall survival in stage I colorectal adenocarcinoma (a) is significantly related to F/B of the primary tumor (p=0.03). F/B of Stage I lung adenocarcinoma is not significantly related to OS (p=0.53). The blue line is Group I has the lowest F/B and the brown line is Group 4 has the highest F/B ratio. Patients at risk at various time points are indicated.

Example 2

Prediction of Fatal Lung Fibrosis

Rationale:
It is not understood why some pulmonary fibroses such as cryptogenic organizing pneumonia (COP) respond well to treatment, while others like usual interstitial pneumonia (UIP) (which may also be referred to as Idiopathic Pulmonary Fibrosis (IPF) are essentially equivalent to each other) do not. UIP and IPF being essentially equivalent for the purposes of the disclosure provided herein. Increased understanding of the structure and function of the matrix in this area is critical to improving our understanding of the biology of these diseases and developing novel therapies. The ability to differentiate between lung fibroses that respond well to therapies and others that are intractable using the methods of the present invention as described herein has profound implications for clinical approaches to treatment and patient care.

Objectives:

Provide new insights into the underlying collagen- and matrix-related biological mechanisms driving COP versus UIP.

Methods:

Two-photon second harmonic generation (SHG) and excitation fluorescence microscopies were used to interrogate and quantify differences between intrinsic fibrillar collagen and elastin matrix signals in healthy, COP, and UIP lung.

Measurements and Main Results:

Collagen microstructure was different in UIP versus healthy lung, but not in COP versus healthy, as indicated by the ratio of forward-to-backward propagating SHG signal ($F_{SHG}/B_{SHG}$). This collagen microstructure as assessed by $F_{SHG}/B_{SHG}$ was also different in areas with preserved alveolar architecture adjacent to UIP fibrotic lesions versus healthy lung. Fibrosis was evidenced by increased col1 and col3 content in COP and UIP versus healthy, with highest col1:col3 ratio in UIP. Evidence of elastin breakdown (i.e. reduced mature elastin fiber content), and increased collagen:mature elastin ratios, were seen in COP and UIP versus healthy.

Conclusions:

Fibrillar collagen's subresolution structure (i.e. "microstructure") is altered in UIP versus COP and healthy lung, which may provide novel insights into the biological reasons why unlike COP, UIP is resistant to therapies, and demonstrates the ability of SHG microscopy to potentially distinguish treatable versus intractable pulmonary fibroses.

Introduction

Pulmonary fibrosis is characterized by accumulation of extracellular matrix (ECM) proteins in lung tissue. The mechanisms leading to pathologic (or non pathologic) accumulation and organization of matrix proteins remain poorly understood. Although we have some insight into the composition, structure and/or organization of the matrix, many properties of the matrix remain uninvestigated. Numerous matrix proteins likely contribute to organ dysfunction in pulmonary fibrosis, however, we are only beginning to understand how homeostasis and organization of these proteins impact cellular function.

Collagen, produced and organized mainly by fibroblasts and scar-forming myofibroblasts, is one of the most abundantly studied matrix proteins. At least twenty-eight different collagen subtypes have been described to date. All collagen species contain three alpha peptide sequences forming a triple helix. Collagen type is determined by the type(s) of alpha peptides and post translational modifications, hydroxylation, and/or glycosylation. Further modification of collagen structure occurs after release into the extracellular space. Here, crosslinking and joining of the helices occur to form collagen fibrils and larger collagen fibers, and fibrosis (aberrant excess deposition of collagen) may occur. The fibril-forming collagens include collagen types 1-3, 5, 11, 24, and 27 (Shoulders M D, Raines R T. Collagen structure and stability. *Annu Rev Biochem* 2009: 78:929-958), and at least several of these fibrillar collagens (FCs) such as types I, II, and V are key players in lung fibroses including usual interstitial pneumonia (UIP) and cryptogenic organising pneumonia (COP) (Cordier J F. Cryptogenic organising pneumonia. *The European respiratory journal: official journal of the European Society for Clinical Respiratory Physiology* 2006:28:422-446. Cottin V, Cordier J F. Cryptogenic organising pneumonia. *Seminars in respiratory and critical care medicine* 2012; 33:462-475.

Parra E R, Teodoro W R, Velosa A P, de Oliveira C C, Yoshinari N H, Capelozzi V L. Interstitial and vascular type v collagen morphologic disorganization in usual interstitial pneumonia. *The journal of histochemistry and cytochemistry: official journal of the Histochemisrry Society* 2006; 54:1315-1325. Parra E R, Kairalla R A, de Carvalho C R, Capelozzi V L. Abnormal deposition of collagen/elastic vascular fibres and prognostic significance in idiopathic interstitial pneumonias. *Thorax* 2007; 62:428-437.). These FCs are also uniquely detectable by Second Harmonic Generation (SHG) Microscopy (SHGM) (details below).

Pulmonary fibrosis results from accumulation of fibroblasts, scar-forming myofibroblasts, and extracellular matrix proteins including collagen, and leads to irreversible loss of lung function. It can be caused by various factors including toxins, radiation exposure, autoimmune disorders, and infection. Idiopathic Pulmonary Fibrosis (IPF) is a severe form of fibrotic lung disease that can progress to respiratory failure and has a prognosis worse than lung cancer. There are currently few effective therapies. UIP is the histopathology underlying IPF and is characterized by heterogeneity of disease and accumulation of fibroblast foci and collagen with an emphasis on collagen type I (col1) over type III (col3) (Cordier J F. Cryptogenic organising pneumonia. *The European respiratory journal: official journal of the European Society for Clinical Respirator, Physiology* 2006; 28:422-446. Parra E R, Teodoro W R, Velosa A P, de Oliveira C C, Yoshinari N H, Capelozzi V L. Interstitial and vascular type v collagen morphologic disorganization in usual interstitial pneumonia. *The journal of histochemistry and cylochemistry: official journal of the Histochemistry Society* 2006; 54:1315-1325), and abnormalities in other matrix molecules including elastin (Parra E R, Kairalla R A, de Carvalho C R, Capelozzi V L. Abnormal deposition of collagen/elastic vascular fibres and prognostic significance in idiopathic interstitial pneumonias. *Thorax* 2007; 62:428-437).

IPF is one of many diseases associated with significant collagen and other matrix protein accumulation. It is the most common of the idiopathic interstitial pneumonias, is increasing in prevalence, and it is a progressive disease that causes significant morbidity and mortality. The median duration of survival from the time of diagnosis is only 2.9 years (Nadrous H F, Ryu J H, Douglas W W, Decker P A, Olson E J. Impact of angiotensin-converting enzyme inhibitors and statins on survival in idiopathic pulmonary fibrosis. *Chest* 2004; 126:438-446.). There are currently few effective FDA approved treatments for IPF, making research into IPF pathogenesis critical.

COP is another of the more common types of fibrotic lung diseases. It is also characterized by accumulation of matrix components resulting in organized areas of granulation tissue in the lung. Components of this pathologic matrix accumulation in COP include col1 and col3 (with an emphasis on col3 over col1, in contrast to UIP), fibronectin, and proteoglycan (Cordier J F. Cryptogenic organising pneumonia. *The European respiratory journal: official journal of the European Society for Clinical Respiratory Physiology* 2006; 28:422-446. Cottin V, Cordier J F. Cryptogenic organizing pneumonia. *Seminars in respiratory and critical care medicine* 2012; 33:462-475). In stark contrast to UIP, COP is a treatable disease with most cases responding to corticosteroids. Although the matrix components of UIP and COP have some similarities, it is unknown why the excess matrix in COP can be reabsorbed or cleared after treatment with corticosteroids while the matrix in UIP is resistant to treatment and resolution (Cordier J F. Cryptogenic organising pneumonia. *The European respirator, journal: official journal of the European Society for Clinical Respiratory Physiology* 2006; 28:422-446).

A growing body of literature supports the roles of matrix organization and structure as important effectors of fibrotic lung disease. ECM components have important mechanobiological properties including the abilities to activate pro-fibrotic cytokines; regulate cell trafficking; and modulate cell activation, proliferation, survival and differentiation (Tschumperlin D J, Boudreault F. Liu F. Recent advances and new opportunities in lung mechanobiology. *J Biomech* 2010; 43:99-107. Tschumperlin D J. Liu F, Tager A M. Biomechanical regulation of mesenchymal cell function. *Current opinion in rheumatology* 2013; 25:92-100) The organization and structure of the ECM, including collagen, also helps regulate availability of and interactions with a large variety of cell-matrix binding sites critical for controlling lung function. These findings further reinforce the notion that in biology, structure is a key determinant of function. Indeed, other data suggests that ECM stiffness regulates key cellular activities that may contribute to IPF (Marinkovic A. Liu F, Tschumperlin D J. Matrices of physiologic stiffness potently inactivate idiopathic pulmonary fibrosis fibroblasts. *Am J Respir Cell Mol Biol* 2013:48:422-430), as well as endogenous lung function (Suki B, Stamenovic D, Hubmayr R. Lung parenchymal mechanics. *Comprehensive Physiology* 2011; 1:1317-1351). Hence, there is heightened interest in the content and structure of the matrix, and how abnormal content and structure may impact lung pathophysiology. For these reasons, we hypothesized that differences in ECM structure, and collagen microstructure in particular, underlie the different natural histories, prognoses, and responses to treatment of UIP and COP.

To explore this question, we used SHGM to compare the matrix of UIP and COP to that of healthy lung tissue. SHGM is a variant of 2 photon (2P) microscopy that detects the FCs without exogenous labels, and can be used to interrogate changes in collagen's macrostructural properties (e.g. collagen fiber density, arrangement, and organization), as well as collagen's subresolution microstructural properties (e.g. the diameter, order versus disorder, and/or packing density of collagen fibrils within larger collagen fibers) (reference Perry S W, Burke R M, Brown E B. Two-photon and second harmonic microscopy in clinical and translational cancer research. Annals of Biomedical Engineering 2012; 40:277-291. Perry S W. Han X, Brown E B. Second harmonic generation in tumors: Scattering and polarization. In: Pavone F S, Campagnola P J, editors. Second harmonic generation imaging. London, UK: Taylor and Francis; 2012. Perry S W. Schueckler J M, Burke K, Arcuri G L, Brown E B. Stromal matrix metalloprotease-13 knockout alters collagen i structure at the tumor-host interface and increases lung metastasis of c57bl/6 syngeneic e0771 mammary tumor cells. *BMC Cancer* 2013; 13:411. Han X, Burke R M, Zettel M L, Tang P. Brown E B. Second harmonic properties of tumor collagen: Determining the structural relationship between reactive stroma and healthy stroma. *Opt Express* 2008; 16:1846-1859. Lacomb R, Nadiarnykh O, Townsend S S, Campagnola P J. Phase matching considerations in second harmonic generation from tissues: Effects on emission directionality, conversion efficiency and observed morphology. *Opt Commun* 2008; 281:1823-1832. Mertz J. Moreaux L. Second harmonic generation by focused excitation of inhomogeneously distributed scatterers. *Optics Communications* 2001; 196:325-330).

These microstructural features of individual collagen fibers, as they can influence SHG directionality from that fiber (i.e. $F_{SHG}/B_{SHG}$, defined below), are herein collectively referred to as collagen "microstructure." In this aspect, SHGM is unique in its ability to interrogate subresolution structure of FCs (e.g. col1 and col3) in intact and potentially live samples without exogenous labels, abilities which also make SHGM an attractive potential clinical and investigational diagnostic tool. Thus this technique can utilize intrinsic properties of matrix components to characterize the content and organization of the ECM in these fibrotic lung diseases.

Using SHGM, herein we describe important differences in matrix content and organization in UIP/IPF and COP compared to healthy lung tissue. Specifically, we found differences in collagen's subresolution structural properties in UIP compared to COP and healthy lung as assessed by SHGM. Importantly, even adjacent normal UIP tissue exhibited these differences in collagen microstructure compared to healthy lung, thus introducing the compelling possibilities that altered collagen microstructure might lead to or correlate with fibrosis in the relatively intractable disease UIP, but not in the more treatable COP. We also report different col1:col3 ratios in UIP versus COP and healthy lung tissue, and other evidence suggests that altered col1:col3 ratios can drive (or perhaps be driven by) changes in PC microstructure such as fibril diameter. Finally, we show both UIP and COP have differences in mature elastin fiber content, and elastin:collagen ratio, suggesting that both fibrotic disease have identifying physiological differences in matrix structure suggestive of lung disease, but only the less tractable disease, UIP, exhibits differences in underlying collagen microstructure. These results are important because they provide new insights into the potential biological and biostructural underpinnings of refractory versus "treatable" lung fibroses, with an emphasis on subresolution collagen microstructure, and demonstrate the potential of the various methods described herein as a powerful new tool for aiding in the diagnosis and treatment of lung fibrosis.

Methods

Histology and Immunohistochemistry:

Paraffin embedded human lung tissue sections were obtained from the Department of Pathology using an RSRB approved protocol after pathological confirmation of either UIP or organizing pneumonia. Healthy lung tissue specimens were obtained from non-smoker subjects who had a lung biopsy for a lesion that was confirmed either benign or not primary lung cancer, from regions adjacent to the lesions that did not contain any portion of the lesion. Hematoxylin-eosin (H&E) staining and immunohistochemistry for col1 and col3 were performed as previously described (Perry S W, Schueckler J M, Burke K, Arcuri G L, Brown E B. Stromal matrix metalloprotease-13 knockout alters collagen i structure at the tumor-host interface and increases lung metastasis of c57bl/6 syngeneic e0771 mammary tumor cells. *BMC Cancer* 2013:13:411).

SHG Microscopy:

Paraffin embedded human lung tissue sections for healthy, UIP and COP were prepared as described above, sectioned, then imaged for forward ($F_{SHG}$) and backward ($B_{SHG}$) SHG signals; col1 and col3 immunofluorescence (IF); and elastin autofluorescence (AF), using a custom-built multi-photon microscope as previously described (Perry S W, Schueckler J M, Burke K. Arcuri G L, Brown E B. Stromal matrix metalloprotease-13 knockout alters collagen i structure at the tumor-host interface and increases lung metastasis of c57bl/6 syngeneic e0771 mammary tumor cells. *BMC Cancer* 2013; 13:411). Images were captured, then F/B SHG ratio ($F_{SHG}/B_{SHG}$) data, coil and col3 IF, or elastin AF, analyzed and quantified with ImageJ as previously described.

Statistical Analyses:

All data are expressed as means+/−SEM. A one way ANOVA was used to establish statistical significance using Graph Pad Prism software. Results were considered significant if p<0.05.

Results

Fibrillar Collagen Microstructure in the ECM is Different in UIP, but not COP, Versus Healthy Lung.

Figure 5:
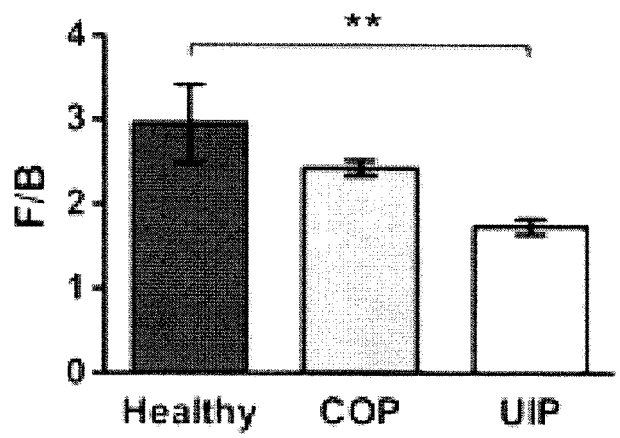
FIG. 5 is a graph depicting differences in F/B ratio for Healthy, COP and UIP lung tissue samples.

SHG in general is sensitive to changes in collagen microstructure including regularity or ordering of collagen fibrils within larger collagen fibers; fibril compaction; and fibril diameter, tilt angle, or pitch angle. SHG is emitted both forwards and backwards (i.e. epi-directed) from the SHG-generating scatterers in the focal volume, and the $F_{SHG}/B_{SHG}$ ratio in particular is primarily sensitive to the spatial extent of SHG-generating scatterers along the optical axis, i.e. the effective diameter or packing arrangement/density/order versus disorder of collagen fibrils within the SHG focal volume. Therefore, to determine if a relatively intractable lung fibrosis such as UIP has a different underlying FC microstructure in the ECM versus a treatable lung fibrosis such as COP, or versus healthy lung, we used SHGM to interrogate the mean $F_{SHG}/B_{SHG}$ ratio in the ECM of UIP, COP, and healthy lung tissues. Intriguingly, we found this $F_{SHG}/B_{SHG}$ ratio was significantly decreased UIP versus healthy lung, but unchanged in COP versus healthy lung (FIG. 5).

Figure 6:
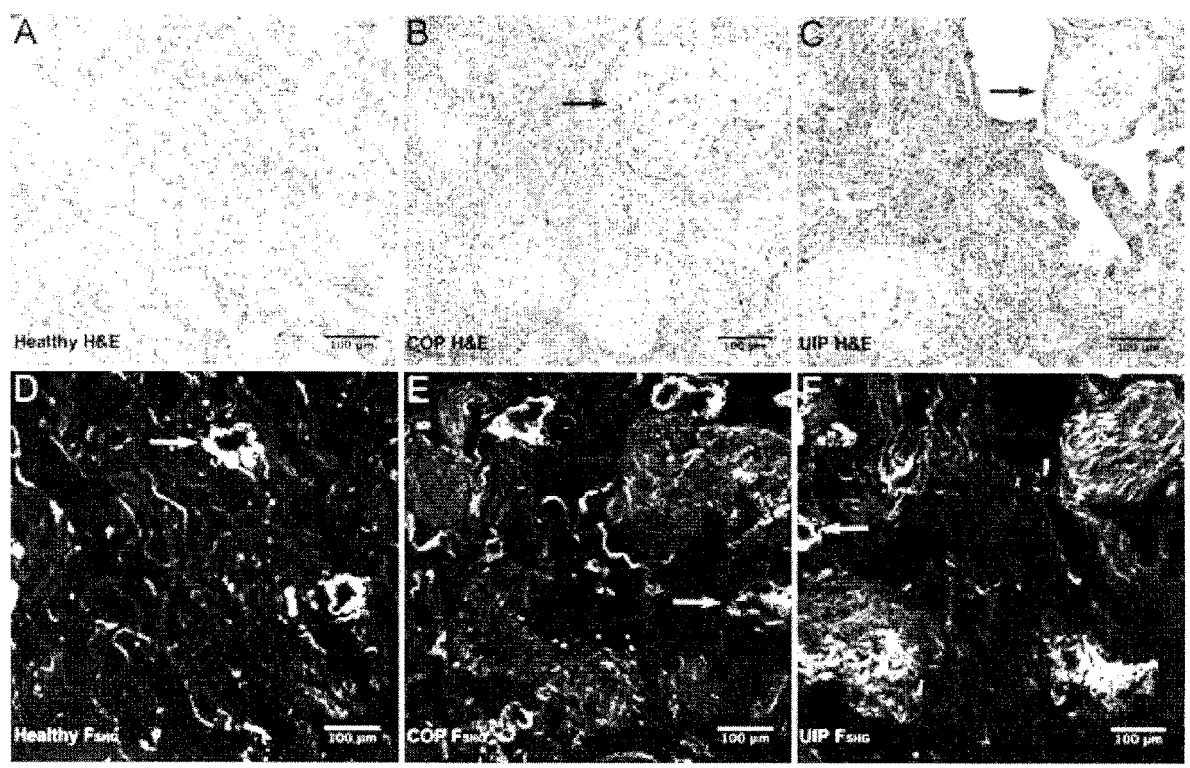
FIG. 6 depicts healthy, COP, and UIP lung histopathology compared to $F_{SHG}$.

FIG. 6 shows representative H&E staining (2A-C) matched to the same fields of view for $F_{SHG}$ (2D-F) for healthy, COP, and UIP respectively, and illustrates that the SHG signal (white pixels, 2D-F) quantified from these lung tissues arises as expected chiefly from small airways (yellow arrows) and parenchymal alveolar space in healthy lung (2A/D), and from fibrotic collagen deposition (blue arrows) in COP (2B/E) and UIP (2C/F).

Together these results show that FC microstructure is altered in UIP but not in COP versus healthy lung.

Figure 7:
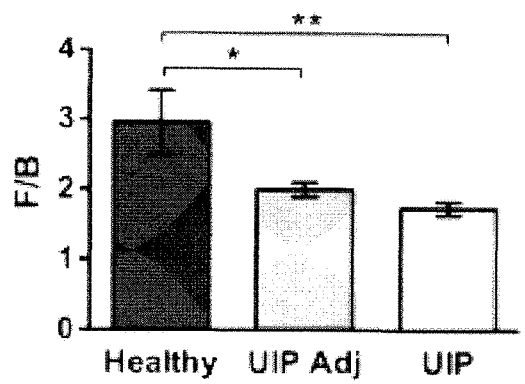
FIG. 7 is a graph depicting differences in F/B ratio for lung tissue with preserved alveolar architecture adjacent to UIP fibrotic lesions compared with Healthy and UIP tissue.

Lung Tissue with Preserved Alveolar Architecture Adjacent to UIP Fibrotic Lesions has Different Fibrillar Collagen Microstructure Versus Healthy Lung Next, we wondered whether lung tissue adjacent to UIP fibrotic lesions with preserved alveolar architecture also had different FC microstructure versus healthy lung as measured by $F_{SHG}/B_{SHG}$, which might suggest the possibility of underlying collagen structural deficits that could predict or predispose development of UIP. Indeed, both fibrotic lesions and surrounding normal appearing lung tissue showed differences in $F_{SHG}/B_{SHG}$ ratio versus healthy lung tissue (FIG. 7). These results provide an exciting, previously unreported "first glance" into the biologic underpinnings of UIP as it relates to FC microstructure, and suggest the possibility that pre-existing alterations in FR microstructure even in "normal" lung tissue may foreshadow or precipitate development of UIP.

Col1, Col3, and Col1/Col3 Ratio Differences in UIP Versus COP and Healthy Lung

Col1 and col3 are implicated in the pathology of UIP and COP, and as fibrotic diseases, col1 and col3 levels in UIP and COP are anticipated to be higher compared to healthy lung. Moreover, previous reports have suggested that coil is the primary collagen deposited in UIP, whereas col3 assumes this role in COP (Cordier J F. Cryptogenic organising pneumonia. *The European respiratory journal: official journal of the European Society for Clinical Respiratory Physiology* 2006; 28:422-446). Importantly, relative col1 and col3 expression levels can interact to regulate aspects of collagen microstructure such as collagen fibril or fiber diameter (Fleischmajer R, Perlish J S, Burgeson R E, Shaikh-Bahai F, Timpl R. Type i and type iii collagen interactions during fibrillogenesis. *Ann N Y Acad Sci* 1990; 580:161-175. Romanic A M, Adachi E, Kadler K E, Hojima Y, Prockop D J. Copolymerization of pn collagen iii and collagen i. Pncollagen iii decreases the rate of incorporation of collagen i into fibrils, the amount of collagen i incorporated, and the diameter of the fibrils formed. *The Journal of biological chemistry* 1991; 266:12703-12709. Cameron G J, Alberts I L, Laing J H, Wess T J. Structure of type i and type iii heterotypic collagen fibrils: An x-ray diffraction study. *J Struct Biol* 2002; 137:15-22).

Conversely, by altering availability of fibroblast (or other effector cell type) binding sites on collagen fibrils, changes in collagen's subresolution fibril microstructure may regulate relative collagen expression levels. Therefore, we wished to determine how changes in $F_{SHG}/B_{SHG}$ ratio (FIG. 5), indicative of altered collagen microstructure in lung ECM, correspond with changes in col1/col3 deposition in UIP, COP, and healthy lung.

We found higher col1 levels in both UIP and COP compared to healthy lung, with UIP showing the highest col1 levels versus COP and healthy (FIG. 8A). Both UIP and COP had similarly elevated col3 levels versus healthy lung (FIG. 8B). Overall, this resulted in relative col1:col3 ratios that were significantly elevated in UIP versus healthy controls, but not in COP versus healthy controls (FIG. 8C). FIG. 8D-F illustrate higher Col3 levels in COP (4E) and UIP (4F) versus healthy (4D), as is shown in 4B. Together, these results demonstrate the expected evidence of fibrosis in both UIP and COP compared to healthy lung controls, and confirm previous observations of higher relative col1:col3 deposition in UIP, versus more abundant col3 over coil deposition in COP (Cordier J F. Cryptogenic organising pneumonia. *The European respiratory journal: official journal of the European Society for Clinical Respiratory Physiology* 2006; 28:422-446). These new results are particularly intriguing because UIP shows both a difference in $F_{SHG}/B_{SHG}$ (i.e. FC microstructure) (FIG. 5) and a difference in col1:col3 ratio (FIG. 8C) versus healthy lung, whereas COP shows neither a difference in $F_{SHG}/B_{SHG}$ nor col1:col3 ratio versus healthy lung. Together, these results suggest a possible relationship between FC microstructure differences and altered col1:col3 ratios in intractable UIP fibrosis, but not in the more treatment responsive COP fibrosis.

Elastin and Elastin:Collagen Ratios Differ in UIP and COP Versus Healthy Lung

In parallel with SHGM imaging, intrinsic tissue autofluorescence representing principally mature lung elastin can be captured simultaneously with SHG (Zipfel W R, Williams R M, Christie R, Nikitin A Y, Hyman B T. Webb W W. Live tissue intrinsic emission microscopy using multiphoton-excited native fluorescence and second harmonic generation. *Proc Natl Acad Sci USA* 2003:100:7075-7080), to provide additional insights into how ECM structure and organization may differ in UIP versus COP. Elastin is another lung ECM component that interacts closely with collagen to regulate lung function (Abraham T, Hirota J A. Wadsworth S, Knight D A. Minimally invasive multiphoton and harmonic generation imaging of extracellular matrix structures in lung airway and related diseases. *Pulm Pharmacol Ther* 2011: 24:487-496. Faffe D S, Zin W A. Lung parenchymal mechanics in health and disease. *Physiol Rev* 2009; 89:759-775. Mijailovich S M, Stamenovic D, Fredberg J J. Toward a kinetic theory of connective tissue micromechanics. *J Appl Physiol* 1993; 74:665-681. Yuan H, Ingenito E P, Suki B. Dynamic properties of lung parenchyma: Mechanical contributions of fiber network and interstitial cells. *J Appl Physiol* 1997; 83:1420-1431; discussion 1418-1429), and is frequently dysregulated in fibrotic lung diseases (Blaauboer M E, Boeijen F R, Emson C L, Turner S M. Zandieh-Doulabi B, Hanemaaijer R, Smit T H, Stoop R, Everts V. Extracellular matrix proteins: A positive feedback loop in lung fibrosis? *Matrix Biol* 2013. Pierce R A, Mariani T J, Senior R M. Elastin in lung development and disease. *Ciba Foundalion symposium* 1995; 192:199-212; discussion 212-194). Elastin's intrinsic autofluorescence captured by two-photon excitation fluorescence (TPEF) microscopy arises from the pyridoxine-based pyridolamine cross-links (Zipfel W R, Williams R M, Christie R, Nikitin A Y, Hyman B T, Webb W W. Live tissue intrinsic emission microscopy using multiphoton-excited native fluorescence and second harmonic generation. *Proc Natl Acad Sci USA* 2003; 100:7075-7080. Deyl Z, Macek K. Adam M, Vancikova O. Studies on the chemical nature of elastin fluorescence. *Biochim Biophys Acta* 1980; 625:248-254) found only in mature elastin fibers (Luisetti M, Ma S, Iadarola P, Stone P J, Viglio S. Casado B, Lin Y Y, Snider G L, Turino G M. Desmosine as a biomarker of elastin degradation in copd: Current status and future directions. *Eur Respir j* 2008; 32:1146-1157), thus making TPEF of elastin a useful indicator for the mature elastin fiber content of lung tissue. Therefore, we captured this signal for the same healthy, UIP, and COP specimens, then quantified and expressed it both by itself and relative to the total FC signal (i.e. total SHG signal, or $F_{SHG}+B_{SHG}$), to see whether there were other underlying differences in ECM structure or organization that we could identify and quantify by SHGM and two-photon excitation fluorescence (TPEF) microscopy. Using this methodology, total mature elastin signal was similarly decreased in both UIP and COP compared to healthy lung tissue (FIG. 9A), and FC:mature elastin ratios (FIG. 9B) were similarly increased in UI P and COP compared to healthy. However, in neither of these parameters was UIP different from COP. Panels 5C-D illustrate the lower FC:mature elastin ratio seen in healthy versus UIP respectively.

These data demonstrate that compared to healthy lung, both fibrotic lung diseases (UIP and COP) are characterized by significant gross physiologic disruptions in ECM structure and organization that can be quantified with non-invasive and non-tissue destructive combined SHG and TPEF microscopy. Yet only the more intractable UIP fibrosis shows evidence of disrupted FC microstructure as interrogated by $F_{SHG}/B_{SHG}$, thus highlighting the compelling possibility that together these techniques may help make clinical distinctions between intractable and treatable lung fibroses.

We use SHGM imaging to identify key differences in the ECM of UIP compared to COP and healthy control lung tissue. UIP and COP were chosen because they are both characterized by increases in matrix proteins, particularly FCs, yet they have contrasting natural histories, responses to corticosteroids, and prognoses. The reasons why UIP is progressive and difficult to treat are not clear. One possible explanation is that there may be a fundamental difference in collagen's content, structure, and/or organization in the UIP ECM that renders collagen more structurally more resistant to degradation in UIP versus COP. We tested this hypothesis using SHGM, a microscopy approach that is sensitive to the intrinsic FC organization and microstructure within the matrix, to confirm whether FC in UIP has different microstructural properties versus COP or healthy lung.

Using this approach, we have demonstrated for the first time that FC microstructure in the ECM of UIP is significantly different from FC microstructure in either COP or healthy control lung tissue, as evidenced by the $F_{SHG}/B_{SHG}$ ratio. Changes in this $F_{SHG}/B_{SHG}$ ratio suggest that there is a significant difference in the density, structure, and/or organization of FC in UIP compared to COP and healthy lung tissue, particularly with regard to the effective diameter or packing arrangement/density of collagen fibrils in the ECM. Further defining the exact nature of these "collagen microstructure" differences will be an important goal of further studies, but these results are compelling by themselves because while previous studies have shown expression changes in several collagen subtypes in fibrotic lung diseases, to our knowledge this is the first report of abnormalities of ECM microstructure—and FC microstructure in particular—in UIP. Still more compelling is the fact that only the intractable fibrosis (UIP) demonstrated significant differences in FC microstructure versus healthy lung, whereas the treatable fibrosis (COP) did not, thus providing we believe the first evidence that alterations in collagen's fundamental underlying structure may contribute to whether or not pulmonary fibroses are treatment responsive. These results provide previously unavailable insights into the biological underpinnings of treatment-resistant pulmonary fibrosis, and also highlight the potential of SHGM as a novel clinical diagnostic and investigational tool for distinguishing between intractable and treatable lung fibroses.

We also found that lung tissue with preserved alveolar architecture adjacent to UIP fibrotic lesions has different FC microstructure than healthy lung, suggesting the possibility that pre-existing alterations in FC structure even in "normal" lung tissue may foreshadow or precipitate (or at minimum, associate with) development of UIP. As expected, both col1 and col3 were elevated in UIP and COP versus healthy lung, with coil deposition being predominant to col3 in UIP, and vice-versa in COP, as has been previously reported (Cordier J F. Cryptogenic organising pneumonia. *The European respiratory journal: official journal of the European Society for Clinical Respiratory Physiology* 2006; 28:422-446). These results are significant in the context of our other results reported herein because it is known that changes in FC ratios, particularly col1:col3 ratios, plays a significant role in regulating collagen fibril diameter (one component of collagen microstructure) (Fleischmajer R, Perlish J S, Burgeson R E, Shaikh-Bahai F. Timpl R. Type i and type iii collagen interactions during fibrillogenesis. Ann N Y Acad Sci 1990; 580:161-175. Romanic A M, Adachi E. Kadler K E, Hojima Y, Prockop D J. Copolymerization of pncollagen iii and collagen i. Pncollagen iii decreases the rate of incorporation of collagen i into fibrils, the amount of collagen i incorporated, and the diameter of the fibrils formed. *The Journal of biological chemistry* 1991:266:12703-12709. Cameron G J. Alberts I L, Laing J H, Wess T J. Structure of type i and type iii heterotypic collagen fibrils: An x-ray diffraction study. *J Struct Biol* 2002; 137:15-22). Similarly, by regulating the availability of fibroblast (or other effector cell type) binding sites on collagen fibrils, changes in collagen's subresolution fibril microstructure could in turn control relative levels of FC expression. In other words, different col1:col3 ratios may in turn drive or be driven by altered collagen microstructure in UIP. Together with the earlier data, these results demonstrate that the ECM of UIP not only contains more collagen (particularly more coil) than the ECM of COP and/or healthy lung tissue, but also that there are significant differences in the subresolution microstructure (i.e. diameter, density, and/or organization) of these collagen fibrils in UIP versus COP and healthy, independent of the absolute amount of collagen deposition in each disease.

Finally, we demonstrated that mature elastin content in both UIP and COP is reduced compared to healthy controls. Elastin's intrinsic autofluorescence originates from pyridoxine-based pyridolamine cross-links (Zipfel W R, Williams R M, Christie R, Nikitin A Y, Hyman B T, Webb W W. Live tissue intrinsic emission microscopy using multiphoton-excited native fluorescence and second harmonic generation. *Proc Natl Acad Sci USA* 2003;100:7075-7080. Deyl Z. Macek K, Adam M. Vancikova O. Studies on the chemical nature of elastin fluorescence. *Biochim Biophys Acta* 1980; 625:248-254) found primarily in mature elastin fibers (Luisetti M, Ma S, Iadarola P. Stone P J, Viglio S. Casado B. Lin Y Y, Snider G L. Turino G M. Desmosine as a biomarker of elastin degradation in copd: Current status and future directions. *Eur Respir J* 2008;32:1146-1157) therefore TPEF of endogenous lung elastin preferentially identifies mature elastin fibers in lung tissue. These results are consistent with the concept that breakdown of mature elastin fibers in the lung, and their "replacement" with often excess deposition of immature elastin fibers and elastin precursors, is believed to contribute to reduced lung function in a variety of pulmonary diseases (Souza A Bd, Santos F Bd, Negri E M, Zin W A, Rocco P R M. Lung tissue remodeling in the acute respiratory distress syndrome. *Jornal de Pneumologia* 2003; 29:235-245). These results are also consistent with numerous reports of apparently increased elastin production, for example increased elastin gene expression and protein expression (Hoff C R, Perkins D R, Davidson J M. Elastin gene expression is upregulated during pulmonary fibrosis. *Connective tissue research* 1999; 40:145-153), as well as increased enzymatic breakdown of mature elastin in COPD and IPF (Skjot-Arkil H, Clausen R E, Nguyen Q H, Wang Y, Zheng Q. Martinez F J, Hogaboam C M, Han M, Klickstein L B, Larsen M R, Nawrocki A, Leeming D J, Karsdal M A. Measurement of mmp-9 and -12 degraded elastin (elm) provides unique information on lung tissue degradation. *BMC pulmonary medicine* 2012; 12:34) in these and other (Stone P J, Konstan M W, Berger M. Dorkin H L. Franzblau C, Snider G L. Elastin and collagen degradation products in urine of patients with cystic fibrosis. *Am J Respir Crit Care Med* 1995; 152:157-162) pulmonary fibroses. In other words, increased elastosis (i.e. breakdown of mature elastin fibers), as has been demonstrated for UIP and COP (Skjot-Arkil H, Clausen R E, Nguyen Q H, Wang Y, Zheng Q, Martinez F J, Hogaboam C M, Han M, Klickstein L B, Larsen M R, Nawrocki A, Leeming D J, Karsdal M A. Measurement of mmp-9 and -12 degraded elastin (elm) provides unique information on lung tissue degradation. *BMC pulmonary medicine* 2012; 12:34), most likely leads to a compensatory increase in elastin production in an (ultimately unsuccessful) effort to restore the mature elastin fibers which have been lost. Hence our results here together with these previous results all support the concept of increased elastin turnover (i.e. synthesis and "deposition" of "immature" elastin components) consequent to loss of mature elastin fibers in UIP and COP, with resultant deficits in pulmonary function. Taken together with our findings on different FC microstructure in UIP but not COP versus healthy lung, these observations on elastin content are especially compelling because they demonstrate that compared to healthy lung, both fibroses (UIP and COP) have significant identifying physiologic disruptions in ECM structure and organization that are quantifiable with non-invasive and non-tissue destructive combined SHG and TPEF microscopy. Yet only the more intractable UIP fibrosis has disrupted FC microstructure identifiable by $F_{SHG}/B_{SHG}$, and thus together these techniques may represent novel clinical diagnostic tools for distinguishing between intractable and treatable lung fibroses.

In summary, using SHG and TPEF microscopy, herein we identify several previously unreported key differences between UIP, COP and healthy lung tissue. The collagen microstructure differences we observed in UI P ECM provide novel insights as to why this pathology may be resistant to many therapies. For example, an ECM and/or collagen fibrils that are more densely packed, more ordered or dis-ordered, and/or more cross-linked may be more resistant to homeostatic turnover and exhibit differences in matrix stiffness that are key to modifying cellular activity of resident cells and activation of pro-fibrogenic cytokines such as transforming growth factor beta (TGF-$\square$. Identifying all the microstructural changes present in UIP and/or the mechanisms that regulate them will be a critical part of our future research. These ongoing studies will seek to determine more specifically exactly what features of collagen's microstructure (e.g. fibril diameter, fibril density, and/or hetero- or homo-typic fibril composition or organization) are different in UIP versus COP and healthy lung, and identify molecular targets that may effect these changes in collagen's underlying microstructure. Although further studies are required to ascertain whether or not the altered FC microstructure as we demonstrate here is an underlying cause of (rather than just associated with) differences in natural history, treatment responsiveness, and/or prognosis between UIP and COP, at a minimum these results introduce the intriguing possibility of using SHG microscopy in accordance with the present invention as a novel clinical biomarker that may help predict treatment responsiveness of idiopathic fibrotic lung disease.

FIGURE LEGENDS

FIG. 5: Fibrillar collagen microstructure is different in UIP, but not COP, versus healthy lung. SHG imaging was performed on healthy, COP, and UIP formalin fixed paraffin embedded human lung tissue, and the $F_{SHG}/B_{SHG}$ ratio was calculated to assess relative differences in FC microstructure. Plot represents mean $F_{SHG}/B_{SHG}$ pixel intensity±SEM averaged over ~12 fields of view (FOV) per patient (4-6 FOV/section from 2-3 sections/patient), from n=5, 3, and 10 patients per group respectively (subject to tissue availability). Z-stacks from each FOV were average intensity projected and background subtracted, $F_{SHG}$ and $B_{SHG}$ collagen signals masked to the same XYZ pixel areas, then divided to calculate the mean $F_{SHG}/B_{SHG}$ value±SEM as previously described. Compared to healthy lung tissue, $F_{SHG}/B_{SHG}$ was significantly decreased only in UIP (**p<003) but not COP. Statistics were performed by one way ANOVA with Holm-Sidak post-hoc test and correction for multiple comparisons against healthy control. All values are in relative arbitrary fluorescent units.

FIG. 6: Healthy, COP, and UIP lung histopathology compared to $F_{SHG}$. Representative hematoxylin and eosin (H&E) FOVs showing healthy (A) versus fibrotic COP (B) and UIP (C) pathology were field-matched to the $F_{SHG}$ images (D, E, F) for the same FOVs, respectively. Note the eosin stained areas of concentrated collagen deposition (light pink color, indicated by blue arrows in B and C) that match areas of high FC $F_{SHG}$ signal intensity (white pixel regions, indicated by blue arrows in E and F) in COP and UIP respectively. In contrast, the $F_{SHG}$ (collagen) signal in healthy tissue (D) arises primarily from alveolar parenchyma and small airway walls (examples of small airway walls are indicated by yellow arrows, in all images). Thus SHG detects and allows quantification of altered microstructure (e.g. FIGS. 5, 7, 9) from both intrinsic normal and pathologic collagen content in lung tissue. Levels (screen stretch) are linear and set the same for all images D-F.

FIG. 7: Lung tissue with preserved alveolar architecture adjacent to UIP fibrotic lesions has different fibrillar collagen microstructure versus healthy lung. SHG imaging of the $F_{SHG}/B_{SHG}$ ratio was performed on healthy, UIP, and lung tissue with preserved alveolar architecture adjacent to UIP fibrotic lesions (UIP Adj), details otherwise as described in FIG. 5. The $F_{SHG}/B_{SHG}$ ratio was significantly decreased in both UIP Adj (*$p<0.04$) and UIP (**$p<0.003$) versus healthy lung tissue, suggesting that even "normal appearing" lung tissue in UIP patients has altered FC microstructure. All values are in relative arbitrary fluorescent units.

Figure 8:
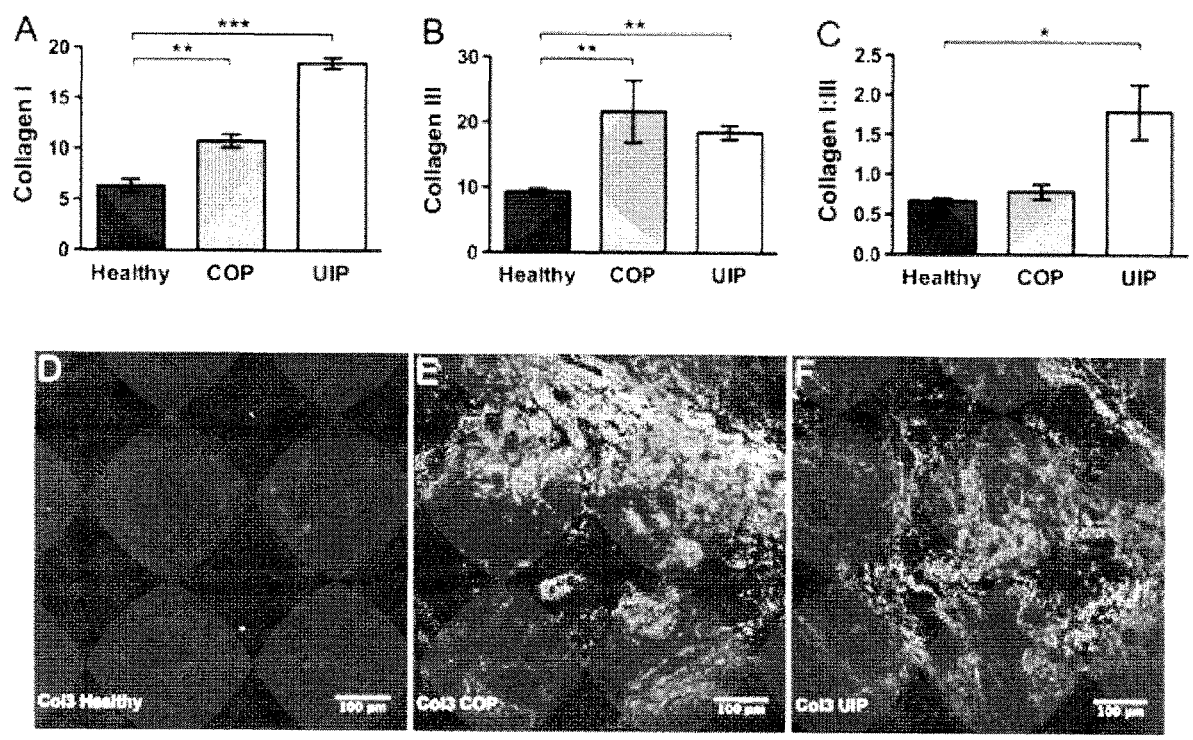
FIG. 8 depicts increased Col1 and Col3 deposition, and Col1:Col3 ratio differences, in UIP or COP versus healthy lung.

FIG. 8: increased Col1 and Col3 deposition, and Col1: Col3 ratio differences, in UIP or COP versus healthy lung. The same patient sets or subsets as described in FIG. 5 were immunofluorescently (IF) labeled for Coil and Col3, and mean IF pixel intensity f SEM quantified for Coil (A), Col3 (B), or Col1:Col3 ratio (C). Z-stacks from each FOV were average intensity projected and background subtracted, and fluorescent intensities from the resultant images were quantified with ImageJ and then expressed as mean anti-Col1 anti-Col3 IF±SEM, as previously described. Col1:Col3 ratio was quantified in the same fashion, then dividing Col1/Col3 signals. Compared to healthy. Col1 deposition was increased in COP ($p<0.004$), and more so in UIP (*$p<0.0001$). Col3 deposition was about equally increased in both COP ($p<0.05$) and UIP ($p<0.005$) versus healthy. Overall, this led to the Col1:Col3 ratio being effectively equivalent in COP versus healthy, but significantly increased in UIP versus healthy (*$p<0.017$). These findings are significant in the context of the $F_{SHG}/B_{SHG}$ changes that were seen in only UIP (but not COP) versus healthy in FIGS. 5 and 6, because altered Col1:Col3 ratios are known to regulate collagen fibril diameter and/or structure (i.e. FC microstructure). Statistics were performed by one way ANOVA with Holm-Sidak post-hoc test and correction for multiple comparisons against healthy control. All values are in relative arbitrary fluorescent units. For illustrative purposes, the originally grayscale Col3 immunofluorescence is shown with "Red" LUT applied in imageJ, with levels (screen stretch) linear and set the same for all images.

Figure 9:
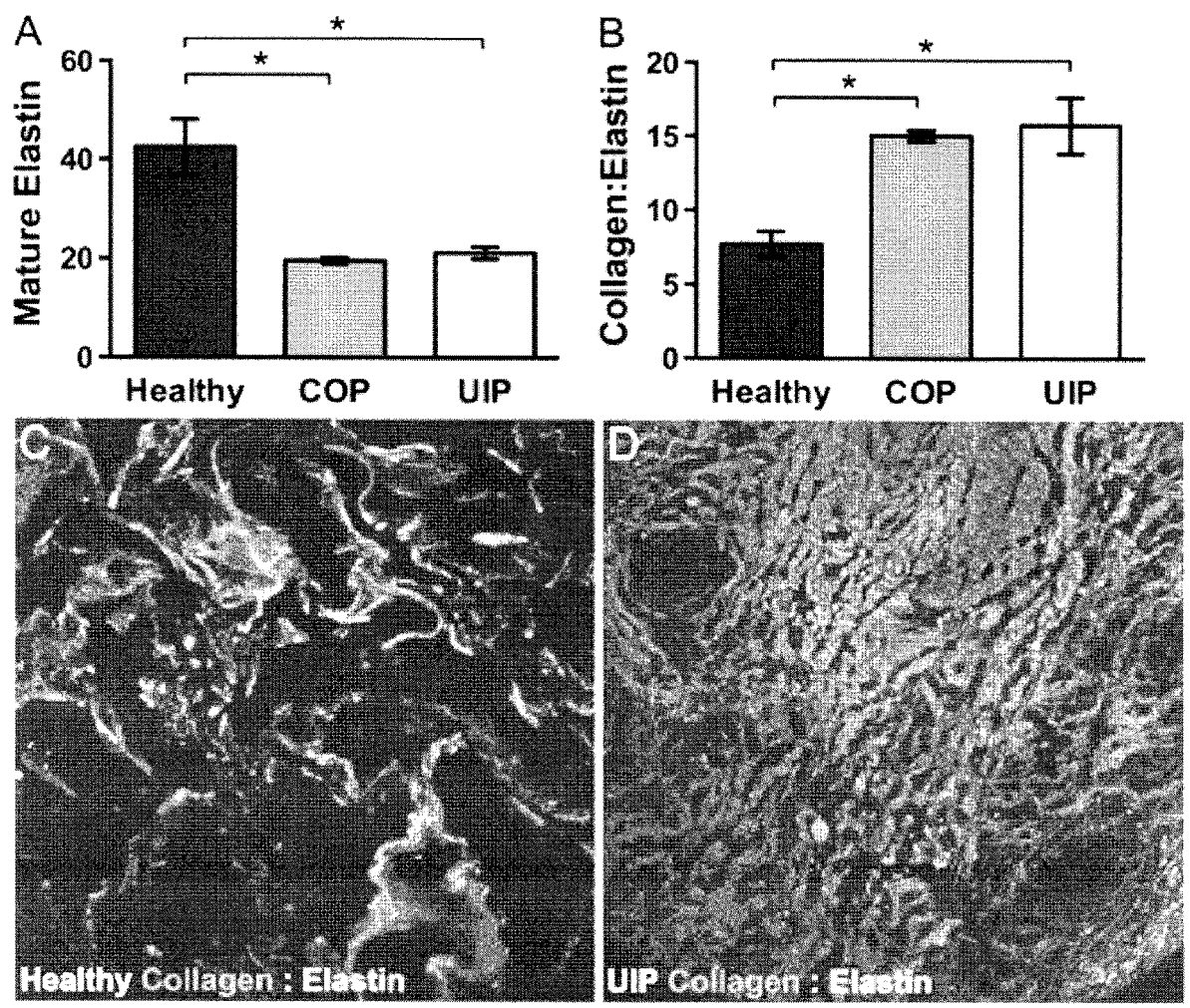
FIG. 9 depicts Elastin and Elastin:Collagen ratio differences in UIP and COP versus healthy lung.

FIG. 9: Elastin and Elastin:Collagen ratios differ in UIP and COP versus healthy lung. The same patient sets or subsets as described in FIG. 5 were imaged and quantified for total FC content (i.e. total $F_{SHG}+B_{SHG}$ signals) and intrinsic autofluorescence from mature lung elastin (captured at 515-555 nm), with the methods as described FIGS. 5, 7, 8 and in Results. Mature elastin fiber content (A) was similarly decreased in both COP (*$p<0.01$) and UIP (*$p<0.01$) versus healthy lung tissue, and the total FC:mature elastin ratio (B) was similarly increased in both COP ($p<0.003$) and UIP ($p<0.003$) compared to healthy. Plots represent mean pixel intensity f SEM for these elastin autofluorescence and $F_{SHG}+B_{SHG}$ signals, and statistics performed by one way ANOVA with Holm-Sidak post-hoc test and correction for multiple comparisons against healthy control. All values are in relative arbitrary fluorescent units. Representative merged images (C) and (D) illustrate this lower total FC SHG (blue):mature elastin (green) ratio seen in healthy compared to UIP (for each image, compare total amount and intensity of the blue summed $F_{SHG}+B_{SHG}$ collagen SHG signal, relative to the green mature elastin signal, in healthy (C) versus UIP (D) panels respectively). For illustrative purposes, the originally grayscale SHG and elastin fluorescence signals are shown with "Blue" and "Green" LUTs applied in ImageJ respectively, with levels (screen stretch) linear and set the same for all channels in all images. Image scale is the same as in FIGS. 6 and 8 above.

Potential Applications

Potential uses for the present invention, as it relates to lung fibrosis, include abilities to:

1. Predict much earlier (i.e. potentially many years earlier) what patients may develop fatal lung fibroses, which may in turn allow: 1. earlier treatment intervention, and/or 2. development of more successful treatments for fatal lung fibroses. Currently there is no way to make such predictions, until diagnosis of fatal lung fibrosis is actually made, e.g. median 2.9 years before death from this disease, at which point it is too late to stop progression of this rapidly fatal disease.

2. Diagnose, with greater certainty, what patients have fatal lung fibrosis (either with bronchoscopy as described in #1 below, or on biopsies as described in #2 below).

3. Provide new insights into etiology and new therapies/treatments for fatal (or other) lung fibroses such as IPF/UIP.

Second Harmonic Generation (SHG) Instrument

The present invention includes an SHG instrument such as a bronchoscope or an SHG instrument in combination with, or in the form of, an endoscope. There are existing commercial confocal bronchoscopes (e.g. CellVizio, Olympus), which could be developed into an SHG bronchoscope. Notably, such an SHG endoscope would have applications for multiple diseases for which collagen SHG and FIB SHG and related readouts may provide clinical diagnostic value. For example, colon and gastrointestinal and gynecological/urological diseases, as well as skin cancer, etc—are disease areas that could all potentially benefit from this method, and for which endoscopy is typically used in diagnostics. A system and Method that enables the measurement of a second harmonic generation forward/backward ratio from an object by performing only a single image scan that may be used with the present invention is disclosed in commonly owned United States Published Patent Application US2013/0057873 A1 entitled "System And Method For Measuring The Ratio of Forward-Propagating to Back-Propagating Second Harmonic-Generation Signal, And Applications Thereof" to Edward Brown III and Xiaoxing Han, the entire disclosure of which is incorporated herein by reference.

Diagnostics

While there is currently "some" ability to "diagnose" UIP/IPF (based on distinguishing features on lung biopsy and/or with High Resolution Computed Tomography (HRCT), family history, etc), currently such diagnoses of "fatal" fibrosis are typically only available and/or made somewhat late in the course of the disease (median survival is 2.9 years after diagnosis, for UIP/IPF). Moreover, there is some uncertainty with the current diagnostic methods, which as noted above include radiologic imaging (HRCT), and/or lung biopsy. In this context, such a SHG bronchoscope or endoscope, as disclosed herein, would provide a less invasive and more certain and/or confirming diagnosis compared to existing (biopsy) methods.

Secondly, our F/B SHG approach could also be applied to clinical diagnostics of lung biopsies for fibroses. This could provide a diagnostic approach with greater certainty than the existing methods (to predict fatal versus non fatal lung fibroses).

Second Harmonic Generation (SHG) and Multiphoton Microscopies Predict and Identify Untreatable Lung Fibrosis Not all lung fibroses are fatal or unresponsive to therapies, but those that are, such as usual interstitial pneumonia (UP), typically progress rapidly with a median survival time of 2.9 years after diagnosis for UIP. It is unknown why some lung fibroses respond well to therapies, yet others like UIP remain intractable and rapidly fatal. Being able to predict, identify, or diagnose earlier which cases may progress to fatal lung fibrosis, before advanced disease onset, may facilitate development or administration of therapies to help "stem the tide" of progressive and fatal lung fibroses.

Fibrosis of the lungs and other tissues is caused by aberrant and excess deposition of collagen, particularly of the fibrillar collagen subtypes. Second Harmonic Generation microscopy (SHGM) and related techniques are a variant of 2 photon (2P) microscopy that can detect (i.e. visualize and assess) these fibrillar collagens in lung (and other) tissues without exogenous labels. As such, SHGM can be used to interrogate changes in collagen's macrostructural properties (e.g. collagen fiber density, arrangement, and organization), as well as changes in collagen's subresolution microstructural properties (e.g. the diameter, order versus disorder, and/or packing density of collagen fibrils within larger collagen fibers). In this aspect, SHGM is unique in its ability to interrogate subresolution structure of fibrillar collagens (e.g. col1 and col3) in intact and potentially live samples without exogenous labels, abilities which also make SHGM an attractive potential clinical and investigational diagnostic tool.

One particular SHGM measure, known as the forward-to-backward SHG ratio, F/B SHG, and/or $F_{SHG}/B_{SHG}$, in particular is primarily sensitive to the spatial extent of SHG-generating scatterers along the optical axis, i.e. the effective diameter or packing arrangement/density/order versus disorder of collagen fibrils within the SHG focal volume. We use the term collagen "microstructure" to refer to these subresolution structural properties of collagen fibrils or fibers, that can influence SHG directionality from that fibril or fiber, to alter the calculated F/B ratio parameter.

In the present invention, we determined that this measurable F/B SHG parameter was different in: 1. Lung tissue with preserved alveolar architecture adjacent to UIP fibrotic lesions (i.e. "adjacent normal" lung tissue) compared to healthy lung (and fibrotic UIP lung tissue had similar F/B to this "adjacent normal" tissue from UIP lung), and 2. Lung tissue from UIP fibrotic lung compared to healthy lung and compared to a non-fatal and "treatable" lung fibrosis, cryptic organizing pneumonia (COP) (which had similar F/B to healthy lung).

These results show for the first time that collagen "microstructure" (i.e. as interrogated by F/B SHG) is different in each of these comparative scenarios, and teach at least two things about the F/B SHG parameter as measured in fibrotic versus normal lung tissues: 1. The F/B SHG parameter may "predict" which lung tissues are likely to become fatally fibrotic (since even normal-appearing, non-fibrotic lung tissue adjacent to fibrotic UIP lung tissue had the same F/B SHG "signature" as the fibrotic UIP lung tissue), and 2. The F/B SHG parameter may "distinguish" fatal lung fibroses from non-fatal lung fibrosis and from healthy lung (since both healthy lung and a non-fatal and treatable lung fibrosis, COP, shared a similar FIB SHG signature, which was different from the F/B SHG signature found in fatal UIP lung tissue).

There are other parameters or "signatures" we can measure in lung tissue with SHG and multiphoton microscopies, such as but not limited to the mature elastin content and the fibrillar collagen:elastin ratio. Both of these parameters were similarly changed in COP and UIP compared to healthy lung tissue, but in neither of these parameters was UIP different from COP.

All together, these data and methods demonstrate that compared to healthy lung, both fibrotic lung diseases studied (i.e. the rapidly fatal and untreatable UIP, and the treatable and non-fatal COP) are characterized by significant gross physiologic disruptions in collagen and extracellular matrix (ECM) structure and organization that can be quantified with non-invasive and non-tissue destructive combined SHG and multiphoton microscopies, as interrogated by the mature elastin content and the fibrillar collagen:elastin ratio parameters. Yet only the more intractable UIP fibrosis shows evidence of disrupted fibrillar collagen microstructure, as interrogated the F/B SHG ratio.

Thus these new methods described above highlight that these techniques, methods and measures, particularly the F/B SHG parameter either by itself and/or in combination with the "mature elastin content" and/or the collagen:elastin ratio measures, may predict onset of, and/or make clinical distinctions between, intractable and treatable lung fibroses.

While the devices, systems and methods disclosed herein are described by way of example as being applied to various cancers and lung fibrosis, they are equally applicable to other diseases where disrupted fibrillar collagen microstructure is an indicator of progression or metastasis of the disease.

It is, therefore, apparent that there has been provided, in accordance with the various objects of the present invention, a method and apparatus for determining the progressive potential of a disease.

While the various objects of this invention have been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of this specification, claims and drawings appended herein.

What is claimed is:

1. A method for predicting a progressive potential of a diagnosed disease, the method comprising the steps of:
   imaging body tissue collagen microstructure using a second harmonic generation instrument;
   measuring a ratio of a forward to backward propagating second harmonic generation signal derived from the imaging of the body tissue collagen microstructure with the second harmonic generation instrument;
   comparing the ratio of the forward to backward propagating second harmonic generation signal to the ratio of the forward to backward propagating second harmonic generation signal of other tissue samples; and
   obtaining the relationship between the ratio of the forward to backward propagating second harmonic generation signal of the imaged body tissue collagen microstructure and metastatic outcome of patients using statistical methods to predict the progressive potential of a diagnosed disease in a patient.

2. The method of claim 1, wherein the statistical methods comprise Kaplan-Meier methods.

3. The method of claim 1, wherein the progressive potential of the disease is a duration of metastasis free survival (MFS).

4. The method of claim 1, wherein the progressive potential of the disease is a duration of progression free survival (PFS).

5. The method of claim 1, wherein the progressive potential of the disease is a metastatic potential for the disease.

6. The method of claim 1, wherein the disease is estrogen receptor positive (ER+) breast cancer.

7. The method of claim 1, wherein the disease is invasive ductal carcinoma.

8. The method of claim 7, further comprising the step of providing adjusted chemotherapy treatment levels to a patient based on a determined progressive potential of their estrogen receptor positive (ER+) breast cancer.

9. The method of claim 1, wherein the disease is colorectal adenocarcinoma.

10. The method of claim 1, wherein the disease is lung fibrosis.

11. The method of claim 1, wherein the method is at least partially performed using a computer.

12. A method for predicting a progressive potential of a disease, the method comprising the steps of:
   imaging in vivo body tissue collagen microstructure using a second harmonic generation instrument in combination with an endoscope;
   measuring a ratio of a forward to backward propagating second harmonic generation signal derived from the imaging of the in situ body tissue collagen microstructure with the second harmonic generation instrument in combination with the endoscope;
   comparing the ratio of the forward to backward propagating second harmonic generation signal to the ratio of the forward to backward propagating second harmonic generation signal of other tissue samples; and
   obtaining the relationship between the ratio of the forward to backward propagating second harmonic generation signal of the imaged in situ body tissue collagen microstructure and metastatic outcome of patients using statistical methods to predict the progressive potential of a diagnosed disease in a patient.

13. The method of claim 12, wherein the progressive potential of the disease is a duration of progression free survival (PFS).

14. The method of claim 12, further comprising the step of predicting a duration of progression free survival (PFS) from the numerical values derived from the ratio of the forward to backward propagating second harmonic generation signal of the imaged in vivo body tissue.

15. The method of claim 12, wherein the progressive potential of the disease is a metastatic potential for the disease.

16. The method of claim 12, wherein the disease is lung fibrosis.

17. The method of claim 12, wherein the disease is a cancer.

18. The method of claim 12, wherein the method is at least partially performed using a computer.

* * * * *